(12) United States Patent
Yang

(10) Patent No.: US 11,317,793 B2
(45) Date of Patent: May 3, 2022

(54) APPARATUS AND METHOD TO ASYNCHRONOUSLY FILL AND PURGE CHANNELS OF ENDOSCOPE SIMULTANEOUSLY

(71) Applicant: ASP Global Manufacturing GmbH, Schauffhausen (CH)

(72) Inventor: Sungwook Yang, Tustin, CA (US)

(73) Assignee: ASP Global Manufacturing GmbH, Schauffhausen (CH)

(*) Notice: Subject to any disclaimer, the term of this patent is extended or adjusted under 35 U.S.C. 154(b) by 0 days.

(21) Appl. No.: 17/469,094

(22) Filed: Sep. 8, 2021

(65) Prior Publication Data

US 2021/0401279 A1 Dec. 30, 2021

Related U.S. Application Data

(60) Division of application No. 16/117,010, filed on Aug. 30, 2018, now Pat. No. 11,134,833, which is a
(Continued)

(51) Int. Cl.
*A61B 1/12* (2006.01)
*A61B 90/70* (2016.01)
(Continued)

(52) U.S. Cl.
CPC .......... *A61B 1/125* (2013.01); *A61B 1/00057* (2013.01); *A61B 1/123* (2013.01);
(Continued)

(58) Field of Classification Search
CPC ..... A61L 2/18; A61L 2/24; A61L 2/28; A61B 1/123; A61B 1/125; A61B 90/70; A61B 1/00057
See application file for complete search history.

(56) References Cited

U.S. PATENT DOCUMENTS 5,279,799 A 1/1994 Moser
6,206,014 B1 3/2001 Cameron, III et al.
(Continued)

FOREIGN PATENT DOCUMENTS

EP 2065059 A1 6/2009
JP 2005-192641 A 7/2005
(Continued)

OTHER PUBLICATIONS

U.S. Appl. No. 16/117,010.
(Continued)

*Primary Examiner* — Sean E Conley
(74) *Attorney, Agent, or Firm* — Frost Brown Todd LLC

(57) ABSTRACT

A method is provided for reprocessing an internal channel of a medical device with a reprocessing system having a valve, a fluid line fluidly coupled with the valve, and at least one sensor coupled with the fluid line. The method includes performing an actuation of the valve to direct liquid through the fluid line and into the internal channel, and detecting with the at least one sensor a predetermined condition within the fluid line while the liquid is being directed into the internal channel. In response to detecting the predetermined condition, a time duration measured from the actuation of the valve is recorded. The method further includes purging the liquid from the internal channel, and directing liquid through the fluid line and into the internal channel for the time duration.

18 Claims, 14 Drawing Sheets

Related U.S. Application Data continuation-in-part of application No. 15/704,276, filed on Sep. 14, 2017, now Pat. No. 10,792,386.

(51) Int. Cl.

| | | |
|---|---|---|
| *A61L 2/18* | (2006.01) | |
| *A61B 1/00* | (2006.01) | |
| *A61B 90/00* | (2016.01) | |
| *A61L 2/24* | (2006.01) | |
| *A61B 17/00* | (2006.01) | |

(52) U.S. Cl.
CPC ............... *A61B 90/70* (2016.02); *A61L 2/18* (2013.01); *A61L 2/24* (2013.01); *A61B 1/00068* (2013.01); *A61B 90/06* (2016.02); *A61B 2017/00119* (2013.01); *A61B 2017/00199* (2013.01); *A61B 2090/064* (2016.02); *A61B 2090/701* (2016.02); *A61B 2090/702* (2016.02); *A61L 2202/122* (2013.01); *A61L 2202/14* (2013.01); *A61L 2202/17* (2013.01); *A61L 2202/24* (2013.01)

(56) References Cited

U.S. PATENT DOCUMENTS

| | | | |
|---|---|---|---|
| 6,585,943 | B1 | 7/2003 | Sanford et al. |
| 6,986,736 | B2 | 1/2006 | Williams et al. |
| 7,479,257 | B2 | 1/2009 | Nguyen et al. |
| 7,686,761 | B2 | 3/2010 | Jackson et al. |
| 7,740,813 | B2 | 6/2010 | Williams |
| 8,246,909 | B2 | 8/2012 | Williams et al. |
| 8,920,574 | B2 | 12/2014 | Bhaumik |
| 10,201,269 | B2 | 2/2019 | Yang et al. |
| 10,702,619 | B2 | 7/2020 | Fang et al. |
| 10,772,491 | B2 | 9/2020 | Chouinard et al. |
| 10,792,386 | B2 | 10/2020 | Yang |
| 2018/0020905 | A1 | 1/2018 | Chouinard et al. |
| 2019/0076009 | A1 | 3/2019 | Yang |

FOREIGN PATENT DOCUMENTS

| | | |
|---|---|---|
| JP | 2010-063610 A | 3/2010 |
| JP | 2010-537735 A | 12/2010 |
| JP | 2012-071030 A | 4/2012 |

OTHER PUBLICATIONS

U.S. Appl. No. 17/009,958.
Extended European Search Report and Written Opinion dated Jan. 24, 2019 for Application No. 181942897. 10 pages.
European Communication dated Oct. 15, 2019 for Application No. 18194289.7, 5 pages.
Partial International Search Report and Written Opinion dated Feb. 14, 2020 for International Application No. PCT/IB2019/000934, 13 pages.
Japanese Office Action, Notice of Reasons for Refusal, dated Aug. 10, 2021 for Application No. JP 2018-171317, 12 pgs.

APPARATUS AND METHOD TO ASYNCHRONOUSLY FILL AND PURGE CHANNELS OF ENDOSCOPE SIMULTANEOUSLY

This application is a divisional of U.S. patent application Ser. No. 16/117,010, entitled "Apparatus and Method to Asynchronously Fill and Purge Channels of Endoscope Simultaneously," filed Aug. 30, 2018, the disclosure of which is incorporated by reference herein, which is a continuation-in-part of U.S. patent application Ser. No. 15/704,276, entitled "Apparatus and Method to Repeatedly Fill and Purge Channels of Endoscope," filed Sep. 14, 2017, now patented as U.S. Pat. No. 10,792,386, issued Oct. 6, 2020, the disclosure of which is incorporated by reference herein.

BACKGROUND

The below discussion relates to the reprocessing (i.e., decontamination) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfectant solution and water rinses. The final rinsing cycle concludes with purging the endoscope channels with compressed air. Optionally, the process may further include an alcohol rinsing cycle in which the endoscope channels are filled with alcohol and then purged with compressed air to facilitate drying of the channels and thereby enhancing the decontamination effects of the process.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

Some versions of reprocessing systems may provide just a single use of a certain volume of disinfectant solution, such that the used volume of disinfectant solution is disposed of after a single use of the volume of disinfectant solution upon completion of the disinfection cycle. Some other versions of reprocessing systems may provide multiple uses of the same volume of disinfectant solution. Specifically, a volume of disinfectant solution may be recovered upon completion of a disinfection cycle and then reused for one or more subsequent disinfection cycles. In some applications, for both single-use disinfectant systems and multi-use disinfectant systems alike, a concentration of the disinfectant may be monitored throughout the process of decontaminating an instrument. For instance, in a multi-use disinfectant system, a concentration level of the multi-use disinfectant may be monitored over the course of multiple disinfection cycles, and the used disinfectant may either re-used or discarded after a given disinfection cycle based at least in part on a remaining concentration of the used disinfectant. Examples of versions of reprocessing systems that provide monitoring and re-use of disinfectant solution are disclosed in U.S. Pat. No. 8,246,909, entitled "Automated Endoscope Reprocessor Germicide Concentration Monitoring System and Method," issued Aug. 21, 2012, the disclosure of which is incorporated by reference herein; in U.S. patent application Ser. No. 15/157,800, entitled "Apparatus and Method for Reprocessing a Medical Device," filed on May 18, 2016, the disclosure of which is incorporated by reference herein; and in in U.S. patent application Ser. No. 15/157,952, entitled "Apparatus and Method to Measure Concentration of Disinfectant in Medical Device Reprocessing system," filed on May 18, 2016, the disclosure of which is incorporated by reference herein.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

Figure 1:
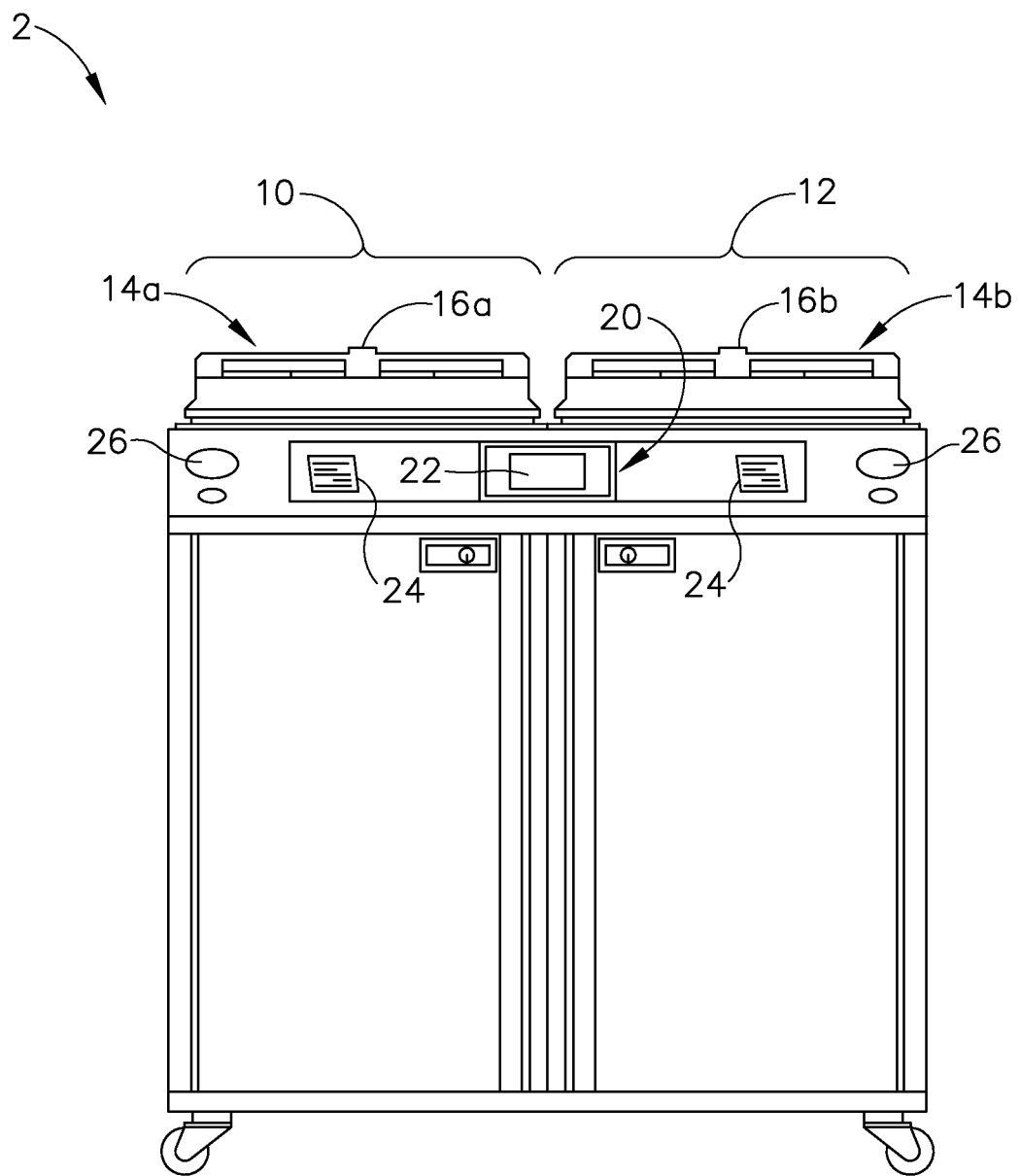
FIG. 1 depicts a front elevational view of an exemplary reprocessing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Figure 2:
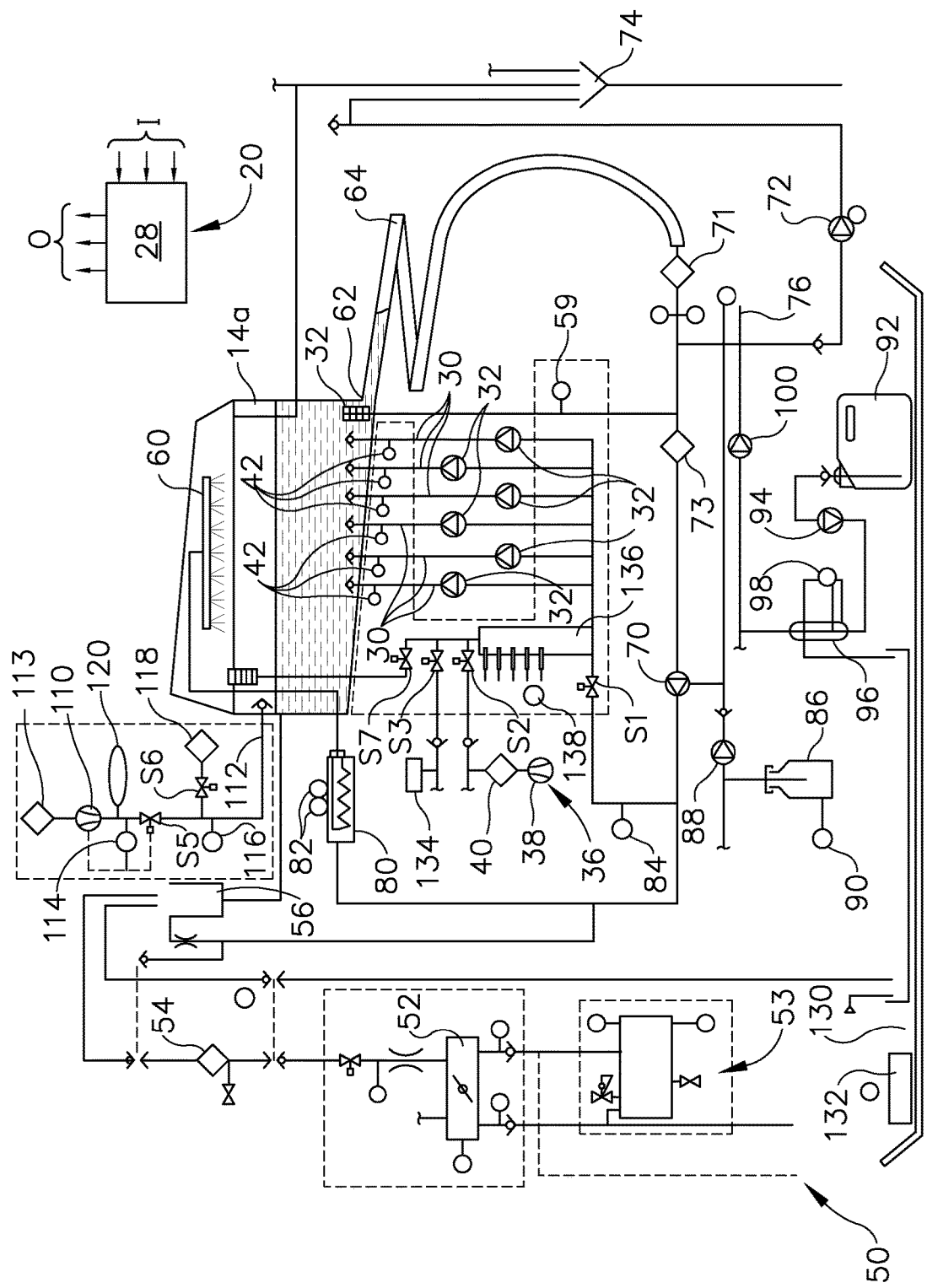
FIG. 2 depicts a schematic diagram of the reprocessing system of FIG. 1, with only a single decontamination basin shown for clarity.

I. Exemplary Medical Device Reprocessing Apparatus with Single-Use Disinfectant FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition, or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow.

Basin (14a) is in fluid communication with a water source (50), such as a utility or tap water connection including hot and cold inlets, and a mixing valve (52) flowing into a break tank (56). A microbe removal filter (54), such as a 0.2 µm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80) with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant (92) is metered into the flow upstream of circulation pump (70) via a metering pump (94). To more accurately meter disinfectant (92), pump (94) fills a metering prechamber (96) under control of a fluid level switch (98) and control system (20). By way of example only, disinfectant solution (92) may comprise an activated glutaraldehyde salutation, such as CIDEX® Activated Glutaraldehyde Solution by Advanced Sterilization Products of Irvine, Calif. By way of further example only, disinfectant solution (92) may comprise ortho-phthalaldehyde (OPA), such as CIDEX® ortho-phthalaldeyde solution by Advanced Sterilization Products of Irvine, Calif. By way of further example only, disinfectant solution (92) may comprise peracetic acid (PAA).

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smoothes out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect subtler blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition, or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (O) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
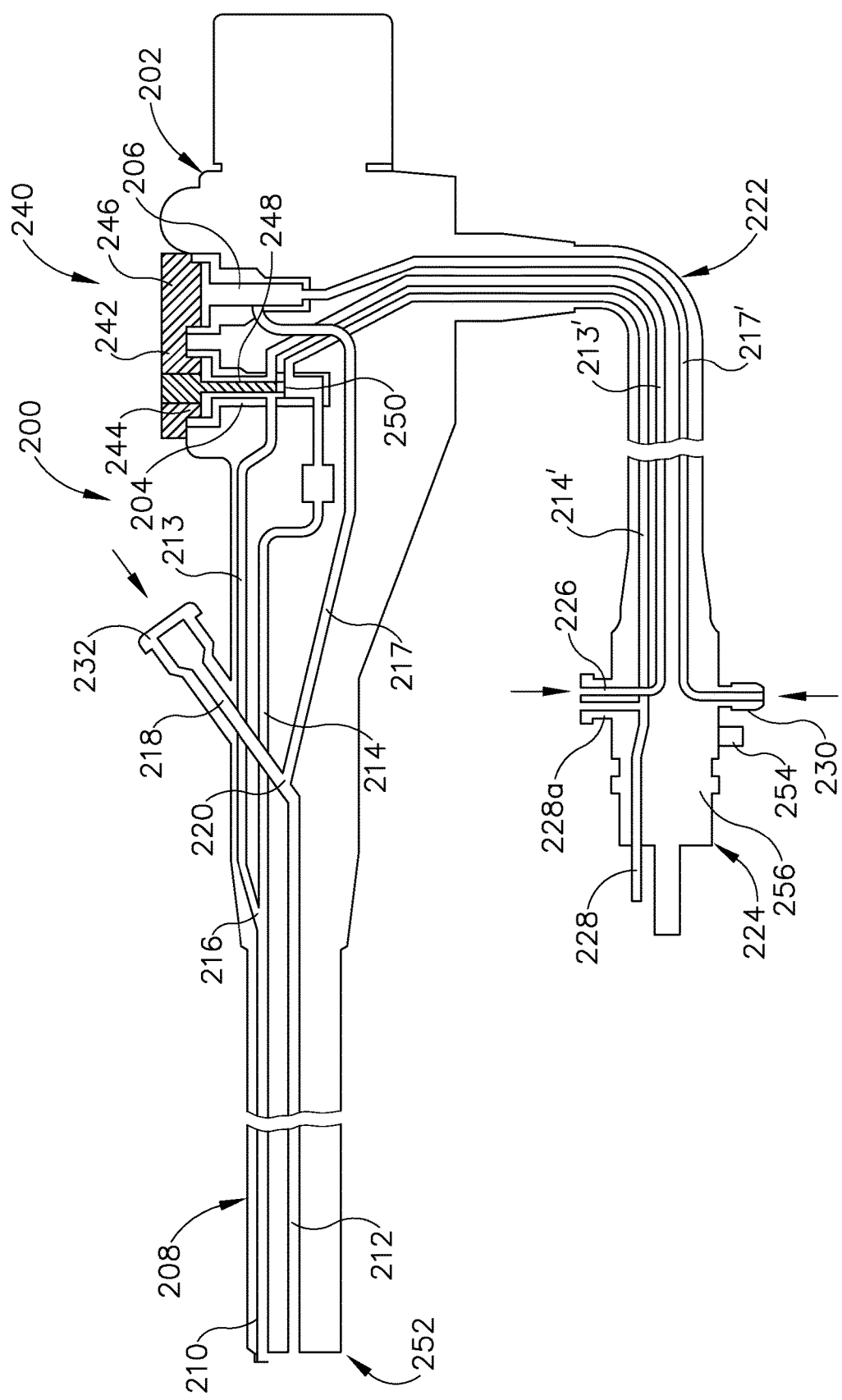
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible shaft (208) is attached to head part (202). A combined air/water channel (210) and a combined suction/biopsy channel (212) are accommodated in shaft (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method with Single-Use Disinfectant In an exemplary use of reprocessing system (2), an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts shaft (208) of endoscope (200) into helical circulation tube (64). End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If the pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfectant solution (92) in basin (14a) is at the in-use concentration prior to circulating through channels (210, 212, 213, 214, 217, 218) of endoscope (200).

Next, a measured volume of disinfectant solution (92) is drawn from disinfectant metering pre-chamber (96) and delivered into the water in basin (14a) via metering pump (100). The volume of disinfectant solution (92) is controlled by the positioning of fill level switch (98) relative to the bottom of metering pre-chamber (96). Metering pre-chamber (96) is filled until fill level switch (98) detects liquid. Disinfectant solution (92) is drawn from metering pre-chamber (96) until the level of disinfectant solution (92) in metering pre-chamber (96) is just below the tip of metering pre-chamber (96). After the necessary volume is dispensed, metering pre-chamber (96) is refilled from the bottle of disinfectant solution (92). Disinfectant solution (92) is not added until basin (14a) is filled, so that in case of a water supply problem, concentrated disinfectant is not left on endoscope (200) with no water to rinse it. While disinfectant solution (92) is being added, channel pumps (32) are off in order to ensure that disinfectant solution (92) in basin (14a) is at the desired in-use concentration prior to circulating through channels (210, 212, 213, 214, 217, 218) of endoscope (200).

The in-use disinfectant solution (92) is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of the disinfectant solution (92) may be controlled by in-line heater (80) to stay at a consistent temperature (e.g., about 52.5° C.). During the disinfection process, flow through each channel (210, 212, 213, 214, 217, 218) of endoscope (200) is verified by timing the delivery of a measured quantity of solution through channel (210, 212, 213, 214, 217, 218). Valve (S1) is closed, and valve (S7) opened, and in turn each channel pump (32) delivers a predetermined volume to its associated channel (210, 212, 213, 214, 217, 218) from metering tube (136). This volume and the time it takes to deliver the volume, provides a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfectant solution (92) is pumped through channels (210, 212, 213, 214, 217, 218), the flow rate through channels (210, 212, 213, 214, 217, 218) is also measured as described above.

At the end of the disinfection cycle, drain pump (72) is activated to remove disinfectant solution (92) solution from basin (14a) and channels (210, 212, 213, 214, 217, 218). During the draining process, sterile air is blown through all channels (210, 212, 213, 214, 217, 218) of endoscope (200) simultaneously to minimize potential carryover.

After disinfectant solution (92) has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 µm filter). The rinse water is circulated within channels (210, 212, 213, 214, 217, 218) by pumps (32); and over the exterior of endoscope (200) via circulation pump (70) and sprinkler arm 60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfectant solution (92) residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Medical Device Reprocessing with Reusable Disinfectant

In some instances, it may be desirable to collect and reuse disinfectant one or more times rather than drain and dispose of the disinfectant after a single use. For example, reusing disinfectant uses less total disinfectant over the useful life of reprocessing system (2) and may thus decrease the overall cost of operation. In addition, concentrated disinfectant, such as the disinfectant provided from disinfectant storage (92), may have a damaging effect on one or more portions of reprocessing system (2) until mixed with water as a disinfectant solution in the desired concentrations. Storing and reusing the disinfectant solution thus reduces the presence of concentrated disinfectant and may thus increase the useful life of reprocessing system (2).

Figure 4:
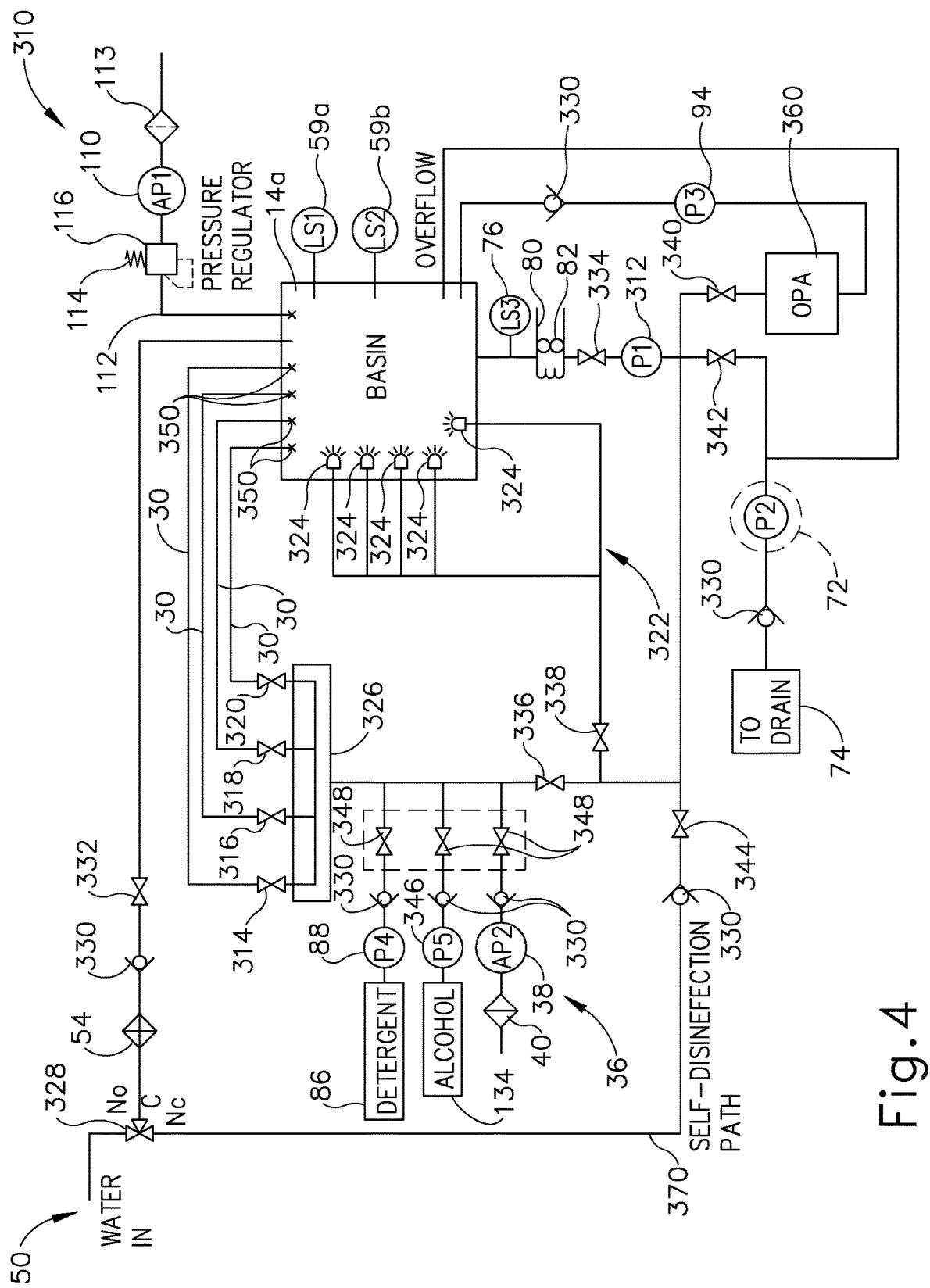
FIG. 4 depicts a schematic diagram of a second exemplary reprocessing system.

FIG. 4 shows an exemplary reprocessing system (310) that has a disinfectant storage reservoir (360) from which to pump the disinfectant to basin (14a) and collect the disinfectant after completion of the disinfection cycle. Alternative versions of reprocessing system (410, 510, 610) discussed herein also include exemplary disinfection storage reservoir (360). It will be appreciated that various aspects of reusing disinfectant may be used with respect to any of reprocessing systems (2, 310, 410, 510, 610) and in any combination as described herein.

As shown in FIG. 4, reprocessing system (310), with second exemplary reprocessing system (310) includes a primary pump (312) that receives the fluid, such as the water and/or disinfectant, and pumps the fluid toward the collection of valves (336, 338, 340, 342, 344) as discussed above with respect to various cycles. More particularly, disinfection valve (340) is configured to transition between a circulation state and a collection state during the disinfection cycle. With disinfection valve (340) in the circulation state, the collection of valves (336, 338, 340, 342, 344) is configured to return disinfectant toward flush lines (30) and nozzle assembly (322) for continued circulation during reprocessing. At the conclusion of the disinfection cycle, disinfection valve (340) transitions from the circulation state to the collection state and, in conjunction with the remaining collection of valves (336, 338, 342, 344), directs the disinfectant into disinfectant storage reservoir (360) for reuse in future disinfection cycles. As used herein, the term "disinfectant" refers to concentrated disinfectant or any solution including disinfectant at any concentration. The term "disinfectant" is thus not intended to unnecessarily limit the invention to a particular concentration or solution of disinfectant.

Reprocessing system (310) further includes disinfectant pump (94) in fluid communication between disinfectant storage reservoir (360) and basin (14a). Disinfectant pump (94) thus pumps the disinfectant directly into basin (14a). Check valve (330) is also fluidly connected between basin (14a) and disinfectant pump (94) and is configured to inhibit fluid within basin (14a) from flowing backward toward pump (94). In some versions, disinfectant storage reservoir (360) is in the form of a break tank such that primary pump (312) and disinfectant pump (94) are configured to individually and/or simultaneously interact with disinfectant storage reservoir (360). However, it will be appreciated that alternative couplings and other features may be used to fluidly couple any form of disinfectant storage reservoir (360) within reprocessing system (310) for collecting and reusing disinfectant. The invention is thus not intended to be limited to the particular disinfectant storage reservoir (360).

Reprocessing system (310) of this example may be readily incorporated into stations (10, 12) (see FIG. 1) with basins (14a, 14b). Basin (14a) shown in FIG. 4 thus receives water from water source (50) and discharges all water therefrom via drain (74), as discussed above. Exemplary basin (14a) includes a plurality of flush lines (30) extending therein and a nozzle assembly (322) having a plurality of nozzles (324). Each flush line (30) and nozzle (324) is configured to direct the water and/or any additive solution, which may be generally referred to as the fluid, toward endoscope (200) (see FIG. 3) within basin (14a) for reprocessing. As discussed above, flush lines (30) are configured to discharge the fluid into respective channels (210, 212, 217, 218) (see FIG. 3), at respective predetermined conduit flow rates particularly configured for each respective channel (210, 212, 217, 218) (see FIG. 3). To this end, primary pump (312) pumps a predetermined supply flow rate of the fluid collectively to flush lines (30) via a common manifold (326) that is fluidly coupled therebetween.

A plurality of flush valves (314, 316, 318, 320) are positioned respectively in each flush line (30) and are collectively configured to balance fluid flow from primary pump (312) such that each flush line (30) discharges fluid therefrom at respective predetermined conduit flow rates. In some versions, flush lines (30) deliver four different respective predetermined conduit flow rates of fluid to channels (210, 212, 217, 218) (see FIG. 3). In some other versions, one or more of the respective predetermined conduit flow rates are approximately equivalent to accommodate an alternative medical device. In any case, any number of flush lines (30) configured to deliver fluid at any predetermined conduit flow rates may be used to accommodate one or more types of medical devices.

Water source (50) delivers the water to a three-way introduction valve (328), which directs the water through filter (54), check valve (330), and two-way valve (332) into basin (14a). As in reprocessing system (2) (see FIG. 2), the water may be collected to a desirable amount as detected by level sensors (59a, 59b, 76). The water drains from basin (14a) and may pass through heater (80) and two-way valve (334) to reach primary pump (312) for distribution toward flush lines (30) and nozzle assembly (322). More particularly a collection of two-way valves (336, 338, 340, 342, 344) are fluidly connected downstream of primary pump (312) to either allow or inhibit fluid flow therethrough for various cycles as discussed herein. For example, flush valve (336) and nozzle valve (338) are configured to control flow respectively toward flush lines (30) and nozzle assembly (322).

In addition, disinfectant valve (340), drain valve (342), and return valve (344) are respectively configured to provide disinfection of endoscope (200), drainage from reprocessing system (310), and self-disinfection of reprocessing system (310). Disinfection and self-disinfection will be discussed below in additional detail. In the present example, disinfection valve (340), drain valve (342), and return valve (344) are presumed fully closed so as to direct the entirety of the predetermined supply flow of the fluid through the opened flush and nozzle valves (336, 338). However, the collection of valves (336, 338, 340, 342, 344) may be fully opened, partially opened, and/or fully closed so as to direct the fluid in any one of a plurality of desirable ratios to complete the cycles of reprocessing. The invention is thus not intended to be limited specifically to the combination of open and/or closed valves as described herein.

Downstream of flush valve (336), additive storages, such as detergent and alcohol storage (86, 134), and detergent metering pump (88), an alcohol metering pump (346), and a gas pump (38) fluidly connect to be received with or in place of water flowing toward flush lines (30). A series of optional two-way valves (348) may be fluidly connected downstream of pumps (88, 346, 38) for additional flow control of various additives. In any case, the fluid, such as water, is received within manifold (326) at the predetermined supply flow rate. As shown in exemplary reprocessing system (310) of FIG. 4, each of the four flush lines (30) fluidly connects to manifold (326) and extends into basin (14a) for connection with channels (210, 212, 217, 218) (see FIG. 3) of endoscope (200). More particularly, each flush line (30) includes a coupling port (350) within basin (14a) that is configured to fluidly seal against endoscope (200) for fluidly coupling channels (210, 212, 217, 218) (see FIG. 3) with respective flush lines (30).

As briefly discussed above, each flush line (30) includes its respective flush valve (314, 316, 318, 320) configured to balance fluid flows along flush lines (30) according to the predetermined conduit flow rates. In some versions, flush valves (314, 316, 318, 320) are in the form of orifice valves that are sized relative to each to each other to create predetermined restriction on the fluid entering manifold (326) according to the predetermined supply flow rate. As the pressure within the manifold (326) distributes equally through flush lines (30), predetermined conduit flow rates of fluid flow through each respective flush valve (314, 316, 318, 320) and discharge from coupling ports (350). Alternatively, flush valves (314, 316, 318, 320) may each comprise a variable valve configured to provide a discrete, predetermined flow rate so that the operator may adjust various flow rates to accommodate differing medical devices in reprocessing system (310).

Furthermore, nozzle valve (338) also receives the fluid, such as water, from primary pump (312) and directs the fluid toward nozzle assembly (322). Each nozzle (324) is generally identical in the present example and configured to discharge fluid onto the exterior of endoscope (200) (see FIG. 3) within basin (14a) at approximately equivalent predetermined nozzle flow rates. To this end, nozzle valve (338) is configured to further balance the predetermined supply flow rate of fluid with flush valves (314, 316, 318, 320) such that each nozzle (324) and fluid line (30) discharges fluid therefrom according to its predetermined conduit flow rate and predetermined nozzle flow rate, respectively. Similar to flush valves (314, 316, 318, 320), nozzle valve (338) may also be a variable valve configured to set to a discrete, predetermined flow rate so that the operator may adjust various flow rates to accommodate differing medical devices in reprocessing system (310). Alternatively, nozzle valve (338) in an open position may provide negligible resistance such that the various predetermined flow rates are balanced simply by restriction in each respective nozzle (324).

In use, reprocessing system (310) receives water from water supply (50) into basin (14a). Alternatively, basin (14a) may receive one of the additives alone or in combination with the water. In any case, the fluid collected within basin (14a) is received within primary pump (312) and pumped therefrom at the predetermined supply flow rate. The collection of valves (338, 340, 342, 344) are generally configured to direct the fluid at the predetermined supply flow rate toward manifold (326) and nozzle assembly (322). The fluid flowing toward manifold (326) may also receive one of the additives, such as detergent, as discussed above in additional detail.

A predetermined portion of the fluid flows into manifold (326), while a remaining predetermined portion of the fluid flows through nozzle valve (338). Flush valves (336) and nozzle valve (338) generate predetermined restriction in each respective flush line (30) in order to direct fluid flow along each flush line (30) with at least two different respective predetermined conduit flow rates. Such predetermined restriction and restriction results in flush valves (336) and nozzle valve (338) apportioning the fluid flow therethrough according to the various predetermined flow rates. For example, flush valves (336) and nozzle valve (338) may be configured to direct fluid along four flush lines (30) with four different respective predetermined conduit flow rates. Once balanced accordingly, the fluid discharges from each coupling port (350) and into respective channels (210, 212, 217, 218) (see FIG. 3) with the predetermined conduit flow rates for reprocessing endoscope (200) (see FIG. 3). It will be appreciated that generating such predetermined flow rates via valves (336, 338) may be used in any cycle of reprocessing described herein and is not intended to limit the invention to any specific reprocessing cycle.

Reprocessing system (310) of the present example includes only one primary pump (312) supplying the predetermined supply flow rate of fluid to each flush line (30) and nozzle (324). However, it will be appreciated that any number of pumps may be used in combination, such as in series or parallel, to direct fluid as discussed above. It will therefore be appreciated that the invention is not intended to unnecessarily be limited to only one primary pump (312). By way of further example only, reprocessing system (310) may be configured and operable in accordance with at least some of the teachings of U.S. patent application Ser. No. 15/157,800, entitled "Apparatus and Method for Reprocessing a Medical Device," filed on May 18, 2016, the disclosure of which is incorporated by reference herein.

Figure 5:
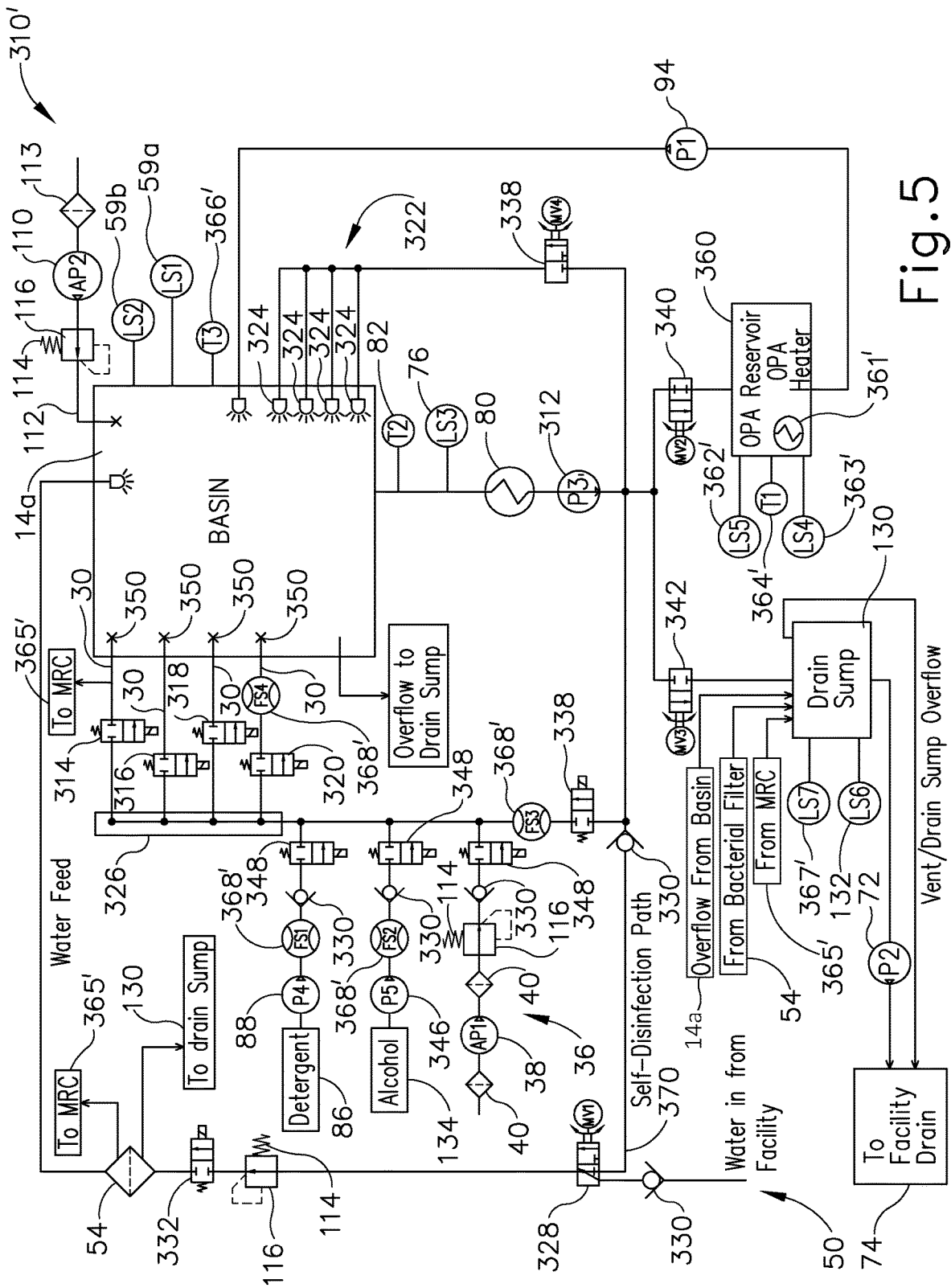
FIG. 5 depicts a schematic diagram of a third exemplary reprocessing system.

FIG. 5 shows another exemplary reprocessing system (310'), which has another exemplary disinfectant storage reservoir (360') fluidly connected between disinfectant valve (340) and pump (94). Disinfectant storage reservoir (360') is generally similar to disinfectant storage reservoir (360) (see FIG. 4), but also includes additional features for further preparing and maintaining the disinfectant for reprocessing. Specifically, disinfectant storage reservoir (360') includes a disinfectant heater (361') that is configured to heat the disinfectant for reprocessing. In some versions, disinfectant heater (361') is configured to pre-heat the disinfectant in anticipation of use in order to more quickly heat the fluid circulating through reprocessing system (310') for reasons discussed below in additional detail. Alternatively or in addition, disinfectant heater (361') may heat the disinfectant while flowing from disinfectant storage reservoir (360') toward pump (94) for use. In either case, disinfectant heater (361') may be configured to heat the fluid in conjunction with heater (80) for collectively heating the fluid as it flows through reprocessing system (310').

Disinfectant storage reservoir (360') further includes a maximum level sensor (362'), a minimum level sensor (363'), and a temperature sensor (364') for monitoring the disinfectant flowing through and/or contained within disinfectant storage reservoir (360'). Maximum and minimum level sensors (362', 363') are configured to approximate the amount of disinfectant contained within disinfectant storage reservoir (360') and communicate with another system, such as control system (20) (see FIG. 1). For example, maximum and minimum level sensors (362', 363') and control system (20) (see FIG. 1) collectively monitor the amount of disinfectant to be above the maximum level, below the minimum level, or between the maximum and minimum levels, which is generally desired for operation. Temperature sensor (364') also communicates with another system, such as control system (20) (see FIG. 1), to monitor the temperature of the disinfectant.

In order to further monitor the disinfectant, reprocessing system (310') also includes a disinfectant concentration measuring subsystem (365') that is configured to receive the disinfectant from at least one location within reprocessing system (310') for sampling and testing. To this end, disinfectant concentration measuring subsystem (365') of the present example receives the disinfectant samples from at least one of flush lines (30). In another example, disinfectant concentration measuring subsystem (365') may receive disinfectant samples from a location downstream of disinfection valve (340). Disinfectant concentration measuring subsystem (365') is configured to test the received samples of disinfectant for a concentration of disinfectant present within the fluid flowing through reprocessing system (310'). In the event that the measured concentration of disinfectant is not within a predetermined range of concentration or is below a predetermined minimum concentration, disinfectant concentration measuring subsystem (365') notifies the operator accordingly. Such measurement and notification may be further aided by communication with control system (20) (see FIG. 1) discussed above in greater detail, which may terminate reprocessing of the instrument. Prior to and following the disinfectant concentration measurement, disinfectant concentration measuring subsystem (365') may be rinsed with water received from an outlet side of filter (54), which water may then drain from subsystem (365') to drain sump (130). As shown in FIG. 5, an inlet side of filter (54) of the present example communicates directly with drain sump (130) via a separate fluid line for removal of air from filter (54).

Upon completion of sampling and testing, the disinfectant drains to drain sump (130) such that disinfectant concentration measuring subsystem (365') is available for further use. It will be appreciated that various devices and method for measuring disinfectant concentration and notifying the operator may be used as described herein and, as such, the invention is not intended to be unnecessarily limited to any particular disinfectant concentration measuring subsystem. By way of further example only, disinfectant concentration measuring subsystem (365') may be configured and operable in accordance with at least some of the teachings of U.S. patent application Ser. No. 15/157,952, entitled "Apparatus and Method to Measure Concentration of Disinfectant in Medical Device Reprocessing System," filed on May 18, 2016, the disclosure of which is incorporated by reference herein.

Additional monitoring is provided in reprocessing system (310') by a basin temperature sensor (366'), a drain sump overflow sensor (367'), and a plurality of flow sensors (368'). Basin temperature sensor (366') is generally configured to measure the temperature of fluid therein, while drain sump overflow sensor (367') is configured to measure an excess of fluid collected within drain sump (130) for alerting the operator and canceling the reprocessing process. Each flow sensor (368') is configured to measure the volumetric flow rate of fluid flowing therethrough for monitoring the overall circulation of fluid through reprocessing system (310'). Each of temperature sensor (366'), drain sump overflow sensor (367'), and flow sensors (368') may communicate with control system (20) (see FIG. 1) for collective operation with any one or more of the sensors discussed herein for using reprocessing system (310). However, it will be appreciated that alternative devices and methods of monitoring reprocessing system (310') may be used and that the invention described herein is not intended to be unnecessarily limited to reprocessing system (310').

IV. Exemplary Medical Device Reprocessing Apparatus and Method for Recurring Flow Cycles In some instances, it may be desirable to increase the bioburden reduction within an internal channel of an endoscope by directing a flow of various solutions, liquids, and/or pressurized air through the endoscope. Although depositing detergents and/or disinfectants within the internal channel of an endoscope may lower the bioburden level of the channels, decreasing the bioburden level in internal channels of endoscopes to a desired level may be particularly difficult due to the small diameters and sometimes irregular profiles of the internal channels. In some cases, simply maintaining a disinfectant or detergent within the internal channels of an endoscope for a specified duration may significantly increase the time required to achieve the desired level of bioburden reduction efficacy. In some instances, an endoscope (200) may include an elevator channel with a cable or wire positioned therein, such as in a duodenoscope. With the presence of a cable or wire contained within the elevator channel, an additional restriction is created as the volume of disinfectant that can flow through the elevator channel is limited. Where the cable is in the form of a twisted cable, numerous gaps and crevices are present that are capable of housing various bioburdens and other particles.

Internal channels (210, 212, 213, 214, 217, 218) of endoscopes (200), and elevator channels of duodenoscopes, may be formed of a material that is more chemical-resistant than the outer surfaces of endoscopes (200). As merely an illustrative example, internal channels (210, 212, 213, 214, 217, 218) may be formed of Teflon or metals that have a higher tolerance to chemical or heat exposure. Accordingly, internal channels (210, 212, 213, 214, 217, 218) are capable of being exposed to a higher concentration of disinfectant or detergent and/or a higher temperature. Additionally, due to the narrow configuration, and sometimes irregular profile, of internal channels (210, 212, 213, 214, 217, 218), utilizing a higher level of concentration may be desirable to effectively achieve bioburden reduction within internal channels (210, 212, 213, 214, 217, 218) due to the greater difficulty in disinfecting internal channels (210, 212, 213, 214, 217, 218) than the outer surface of endoscope (200).

Reprocessing apparatuses that alternate between directing varying treatment solutions through an endoscope (200) may be desirable to increase the bioburden reduction efficacy of the internal channels (210, 212, 213, 214, 217, 218). Providing a recurring cycle where various liquids, detergents, and disinfectants flow through internal channels (210, 212, 213, 214, 217, 218) of endoscopes (200) may be beneficial to lower the bioburden level within the channel (210, 212, 213, 214, 217, 218). As these types of liquids flow reiteratively through internal channels (210, 212, 213, 214, 217, 218), a shear stress is generated on the inner walls of internal channels (210, 212, 213, 214, 217, 218) proportional to the flow rate. This shear stress has a destructive effect on bioburden residing on the channel walls. Thus, it may be desirable to direct pressurized air through internal channels (210, 212, 213, 214, 217, 218) to increase the flow rate of the liquid and displace the liquid contained therein to achieve higher shear stresses and consequently greater bioburden reduction effects. The flow rate of the liquid in the channel (210, 212, 213, 214, 217, 218) significantly increases as more liquid is displaced with air. The amount of flow rate is inversely proportional to the length of channels (210, 212, 213, 214, 217, 218), as demonstrated in the Hagen-Poiseuille's equation provided below:

$$Q = \frac{dV}{dt} = v\pi R^2 = \frac{\pi R^4}{8n}\left(-\frac{\Delta P}{\Delta x}\right) = \frac{\pi R^4}{8n}\frac{|\Delta P|}{L};$$

where in compatible units (e.g., SI): "Q" is the volumetric flow rate; "V(t)" is the volume of the liquid transferred as a function of time, "t"; "v" is mean fluid velocity along the length of the tube; "x" is the distance in direction of flow; "R" is the internal radius of the tube; "ΔP" is the pressure difference between the two ends; "n" is the dynamic fluid viscosity; and "L" is the length of the tube. In various applications, the fluid pressure in the channel may be limited to approximately 30 psi to prevent damage to the channel walls.

In this instance, the shear stress of the inner wall is increased and the amount of bioburden removal is enhanced. The amount of shear stress is proportional to the flow rate, as shown by the following formula $$\tau = \frac{32\mu}{\pi D^3}Q; \tag{3}$$

where "μ" is the viscosity of water and "Q" is the flow rate.

Repeatedly directing a stream of pressurized air through the internal channels (210, 212, 213, 214, 217, 218), once a detergent or disinfectant solution has passed therethrough, may be further desirable to flush the remaining liquid out of endoscope (200) to ensure any remnants from a prior cycle is substantially removed. By repeatedly filling and purging the internal channels (210, 212, 213, 214, 217, 218) of an endoscope (200), the total time required to remove a certain level of bioburden may be reduced; and in any subsequent cycle introducing a high concentration of disinfectant, that disinfectant is less likely to be diluted by residual fluid in channels (210, 212, 213, 214, 217, 218). The following description provides various examples of a reprocessing system that is configured to deliver a reiterative cycle of various substances and solutions to the internal channels of a medical instrument. A reprocessing system may include a single pump assembly that is configured to deliver the various substances, such as detergent, water, pressurized air, etc. In this instance, the reprocessing system may be configured to selectively open and close a series of valves to individually deliver the various substances through the single pump assembly. Alternatively, as shown below, a reprocessing system may include a separate, dedicated pump to deliver each varying substance to internal channels (210, 212, 213, 214, 217, 218). Although individual pumps are described below, it should be understood that a single pump system or pump assembly may be utilized to implement the reprocessing methods detailed below.

A. Medical Device Reprocessing Apparatus and Method Using Pre-Diluted Disinfectant In some instances, as previously discussed above, it may be desirable to use the same disinfectant for multiple disinfection cycles of the internal channels (210, 212, 213, 214, 217, 218) of an endoscope (200). As used herein, the term "disinfection cycle" refers to one instance of filling an internal channel (210, 212, 213, 214, 217, 218) with disinfectant and subsequently purging the disinfectant from the internal channel. A disinfection cycle is thus one variant of a fill and purge cycle (which may also be referred to as a "purge and fill cycle") implemented during the reprocessing of internal channels (210, 212, 213, 214, 217, 218) of an endoscope (200). While fill and purge cycles are described herein primarily in the context of the disinfection stage of instrument reprocessing, during which multiple disinfection cycles may be completed, fill and purge cycles may also be implemented throughout other stages of instrument reprocessing, such as during a washing and rinsing stage.

Performing multiple disinfection cycles for a given internal channel (210, 212, 213, 214, 217, 218) using the same volume of disinfectant may be desirable to provide adequate disinfection of the internal channel while reducing the need for additional disinfectant for each subsequent disinfection cycle. Reutilizing disinfectant for multiple disinfection cycles may thus minimize costs while achieving a sufficient level of biocidal activity. During each subsequent disinfection cycle following an initial disinfection cycle, the dilution factor of the disinfectant may decrease dramatically. The concentration of the disinfectant in the channel (210, 212, 213, 214, 217, 218) can be estimated using the following formula: $C_n = C_i - (C_i \times R^n)$, where "$C_n$" is the disinfectant concentration in the channel after "n" number of purge and fill disinfection cycles; "$C_i$" is the initial undiluted disinfectant concentration; and "R" is the remaining percentage of fluid in the channel after purging. The table below shows the channel disinfectant concentration at different parameters:

| Number of Purge & Fill | Remaining % 10% | Remaining % 20% | Remaining % 30% | Remaining % 40% | Remaining % 50% |
| --- | --- | --- | --- | --- | --- |
| 1 | 90 | 80 | 70 | 60 | 50 |
| 2 | 99 | 96 | 91 | 84 | 75 |
| 3 | 99.9 | 99.2 | 97.3 | 93.6 | 87.5 |

The following description provides various examples of a reprocessing system and method configured to adequately decontaminate the internal channels (210, 212, 213, 214, 217, 218) of an endoscope (200) through a recurring disinfection cycles. Ultimately, providing a methodical approach to disinfecting the inner components of an endoscope (200) may be beneficial to ensure the proper degree of bioburden reduction is achieved in each instance. It should be understood that the reprocessing method described below may be readily incorporated into any of the various reprocessing systems (2, 310, 310') and to any of the various endoscopes (200) described above. Other suitable ways in which the below-described reprocessing method may be used will be apparent to those of ordinary skill in the art in view of the teachings herein.

Figure 6:
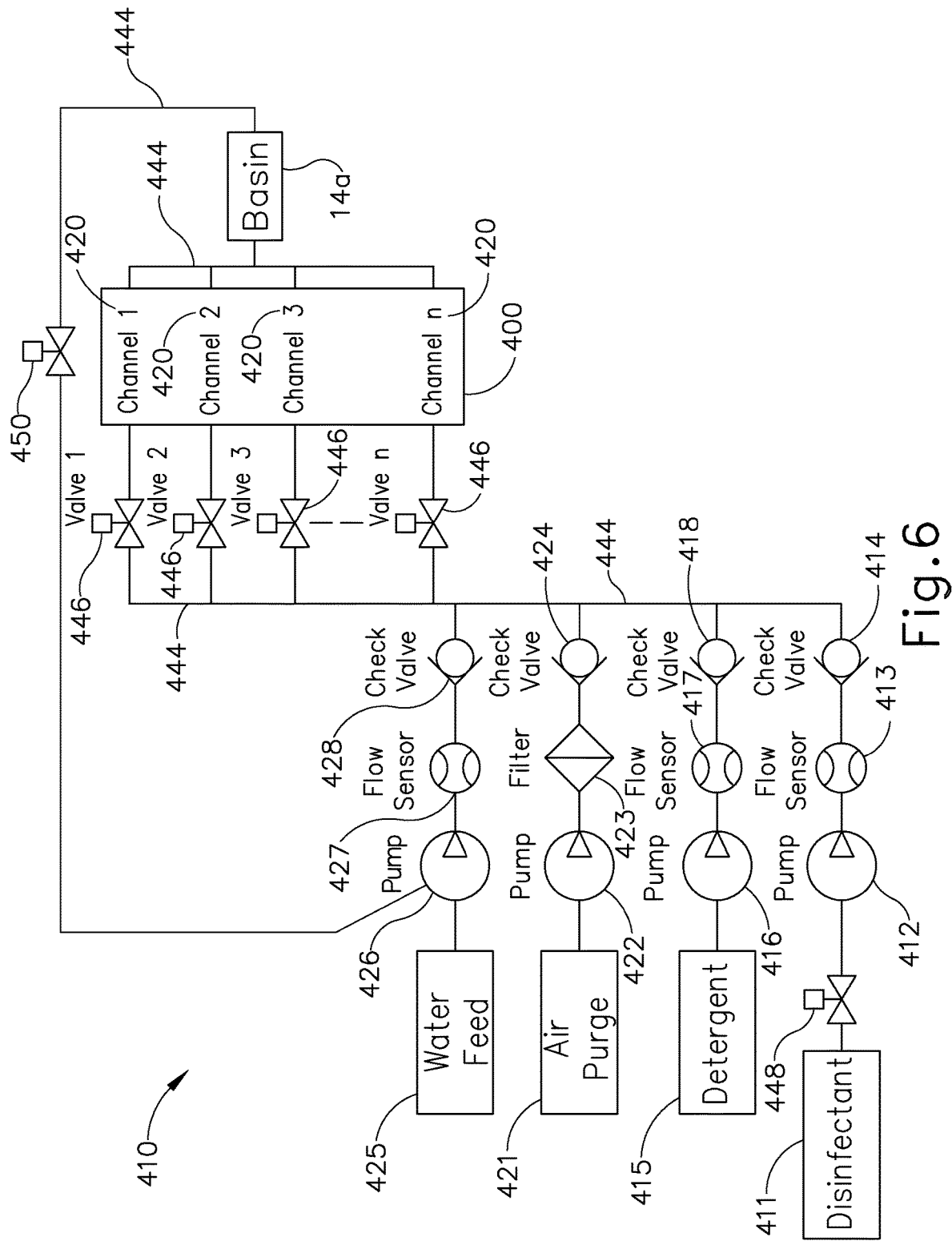
FIG. 6 depicts a partial schematic diagram of an exemplary variation of the reprocessing systems of FIGS. 4-5.

FIG. 6 shows a block schematic of an exemplary reprocessing system (410) including a disinfectant storage (411), a detergent storage (415), an air supply system (421), and a water supply (425). Except as otherwise described below, reprocessing system (410), disinfectant storage (411), detergent storage (415), air supply system (421), and water reservoir (425) are configured and operable just like reprocessing system (2, 310, 310'), disinfectant storage (92, 360), disinfectant (86), air supply system (36), and water supply (50), respectively, described above. Internal channels (420) of an endoscope (400) are in fluid communication with disinfectant storage (411), detergent storage (415), air supply system (421) and water reservoir (425) via flush lines (444). Reprocessing system (410) is operable to deliver disinfectant solution (92), detergent solution (86), air and water to internal channels (420) of endoscope (400) individually and sequentially. While only one endoscope (400) is shown as being reprocessed in reprocessing system (410), it should be understood that reprocessing system (410) may be capable of reprocessing more than one endoscope (400) simultaneously and/or in a sequence.

Flush lines (444) include a flush valve (446) for each channel (420) operatively connected to reprocessing system (410). Flush valves (446) are positioned downstream of disinfectant storage (411), detergent storage (415), air supply system (421), and water reservoir (425). In the present example, disinfectant storage (411) is in fluid communication with a disinfectant pump (412), a flow sensor (413) and a check valve (414) in sequence, such that disinfectant pump (412) is configured to transfer disinfectant (92) from disinfectant storage (411) to flow sensor (413) and through check valve (414) via flush lines (444). In this instance, disinfectant solution (92) is a high concentrate disinfectant that is capable of providing adequate bioburden reduction within internal channels (420).

Flow sensor (413) is operable to monitor the flow of concentrated disinfectant (92) delivered from disinfectant pump (412) to internal channels (420) of endoscopes (400). Control system (20) of reprocessing system (410) is configured to execute a control algorithm (see FIG. 7) to open flush valve (446), which is in fluid connection with endoscope (400), and retrieve the data monitored by flow sensor (413). Control system (20) is operable to terminate fluid communication between disinfectant pump (412) and endoscope (400) when the data obtained from flow sensor (413) indicates that internal channel (420) has received a sufficient amount of concentrated disinfectant (92) by closing off flush valve (446).

Similarly, detergent storage (415) is in fluid communication with a detergent pump (416), a flow sensor (417) and a check valve (418) in sequence, such that detergent pump (416) is configured to transfer detergent solution (86) to flow sensor (417) and through check valve (418) via flush lines (444). Flow sensor (417) is operable to monitor the elapsed duration as detergent (86) is delivered from detergent pump (416) to internal channels (420) of endoscope (400). Reprocessing system (410) is configured to terminate the fluid communication between detergent pump (416) and flush valve (446) once the elapsed duration as monitored by flow sensor (417) has reached a predetermined time threshold. Alternatively, or in conjunction, reprocessing system (410) is configured to cease operation of detergent pump (416) from pumping detergent (86) to internal channels (420). In each instance, reprocessing system (410) is configured to close flush valve (446) when internal channel (420) has received a sufficient amount of detergent (86) therein, as sensed by flow sensor (417).

Air supply system (421) is in communication with an air pump (422), a filter (423) and a check valve (424). Air pump (422) is configured to push pressurized air from air supply system (421) through filter (423) and check valve (424), thereby delivering a stream of air into and through internal channels (420) of endoscope (400). Filter (423) is operable to filter and remove microbes from the incoming air stream extracted from air supply system (421). In some illustrative examples, filter (423) comprises a HEPA microbe-removing filter. In some versions, reprocessing system (410) may exclude filter (423) in communication with air pump (422) and check valve (424). Water reservoir (425) is in fluid communication with a water pump (426), a flow sensor (427) and a check valve (428). Water pump (426) is configured to pump water from water reservoir (425) to flow sensor (427) and through check valve (428) via flush lines (444). Reprocessing system (410) is operable to measure the quantity of water delivered from water pump (426) to internal channel (420) of endoscope (400), based on data from flow sensor (427). Reprocessing system (410) is further configured to close flush valve (446) upon determining that internal channel (420) has received a sufficient amount of water therein, as sensed by flow sensor (427).

Reprocessing system (410) further includes basin (14*a*) in fluid communication with internal channels (420) of endoscope (400) via flush lines (444). Basin (14*a*) is operable to receive any fluids or air released from internal channels (420). Further, basin (14*a*) is in fluid communication with water pump (426) via an independent flush line (444) such that water pump (426) is operable to draw the released fluids within basin (14*a*), which may include disinfectant (92), to water pump (426). In that regard, it will be appreciated that water pump (426) of the present version may be configured to direct fluids to internal channels (420) at higher flow rates than disinfectant pump (412), such that water pump (426) is better suited to recirculate fluids than disinfectant pump (412). In the present version, released fluid is recycled through reprocessing system (410) when water pump (426) activates to pump the released fluid, such as disinfectant (92), and optionally a new volume of water, through flow sensor (427), check valve (428) and into internal channels (420). For example, with basin (14*a*) holding previously used disinfectant (92) recently released from internal channels (420), basin (14*a*) is operable to transfer the previously used disinfectant (92) through flush line (444) to water pump (426) for reuse. In this instance, water pump (426) is configured to pump the previously used disinfectant (92) and any new water into internal channels (420) for an additional disinfection cycle. Simultaneously, disinfectant pump (412) may be configured to obtain a new volume of disinfectant (92) from disinfectant storage (411) for mixture and delivery with the previously used disinfectant (92) being delivered from basin (14*a*) to internal channels (420) by water pump (426). Though not shown, in an exemplary alternative configuration disinfectant pump (412) may be suitably configured to recirculate disinfectant (92) received from basin (14*a*). In such case, disinfectant pump (412) may be fluidly connected with basin (14*a*) via a flush line similar to flush line (444), which may include a proportional valve similar to valve (450) described below.

As seen in FIG. 6, reprocessing system (410) includes a first variable valve (448) (also referred to as a "proportional valve") in line between disinfectant storage (411) and disinfectant pump (412) and a second variable valve (450) (or "proportional valve") between basin (14*a*) and water pump (426). Reprocessing system (410) is operable to selectively open and close variable valves (448, 450) to draw disinfectant (92) from disinfectant storage (411) and separately, or simultaneously, pull fluid from basin (14*a*), respectively. For instance, with first variable valve (448) in an open state and with second variable valve (450) in a closed state, disinfectant pump (412) pulls fresh disinfectant (92) from disinfectant storage (411) and water pump (426) pulls water from water feed (425) without pulling fluids from basin (14*a*). With first variable valve (448) in a closed state and with second variable valve (450) in an open state, water pump (426) pulls fluids from basin (14*a*), including recycled disinfectant (92), and disinfectant pump (412) does not pull fresh disinfectant (92) from disinfectant storage (411).

In some versions, reprocessing system (410) is configured to maintain variable valves (448, 450) simultaneously open. In this instance, unlike flush valves (446), variable valves (448, 450) include variable orifices that are configured to be selectively adjusted. Reprocessing system (410) is configured to adjust the size of the orifice of variable valves (448, 450) to thereby selectively control the amount of disinfectant (92) pulled from disinfectant storage (411) by disinfectant pump (412) and the amount of released fluids drawn from basin (14*a*) by water pump (426). In this instance, reprocessing system (410) is operable to cooperatively manipulate the opening dimensions of variable valves (448, 450) to thereby deliver varied doses and/or concentrations of disinfectant (92) to internal channels (410) during subsequent disinfecting cycles. Although not shown, it should be understood that reprocessing system (410) may include a single pump assembly such that the same pump assembly is configured to deliver detergent (86), water, pressurized air, and disinfectant (92). In this instance, reprocessing system (410) is configured to selectively open and close a series of flush valves (446) to individually deliver the various substances with the single pump assembly.

Figure 7:
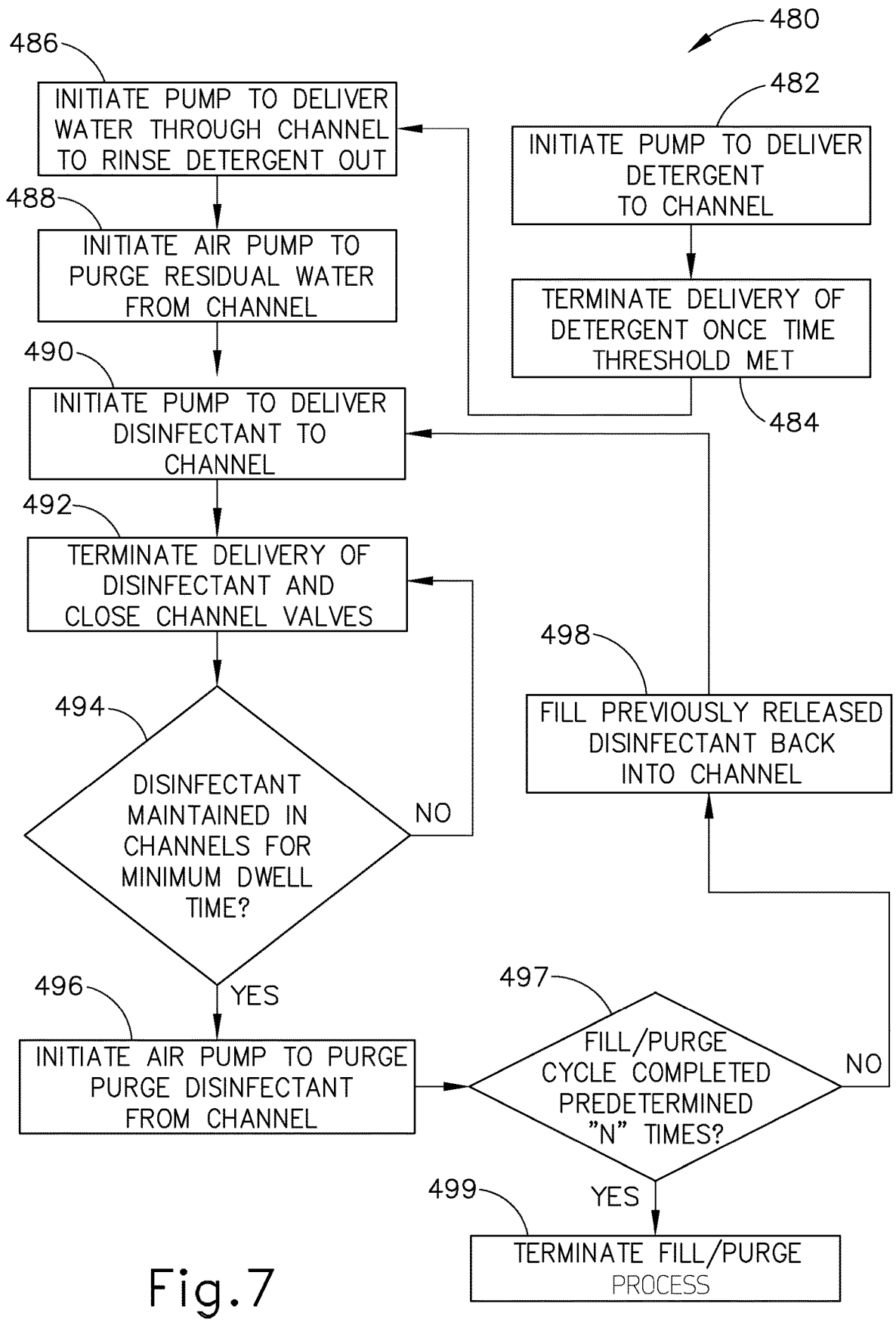
FIG. 7 depicts a flow diagram illustrating an exemplary reprocessing method utilized by the reprocessing system of FIG. 6, with the internal channels of an endoscope undergoing a disinfection stage during which the internal channels are filled and purged with disinfectant multiple times.

FIG. 7 shows a flow diagram illustrating steps of an exemplary reprocessing method (480) that may be used by reprocessing system (410) to perform a predetermined number of fill and purge cycles of internal channels (420) of endoscope (400). At step (482), reprocessing system (410) initiates detergent pump (412) to deliver detergent solution (86) to endoscope (400) via flush lines (444). Reprocessing system (410) is configured to deliver detergent (86) through internal channels (420) at a predetermined flow rate. At step (484), as detergent (86) is transferred from detergent storage (415) to endoscope (400), flow sensor (417) measures an elapsed duration of flow as detergent pump (416) actively pumps detergent (86) toward internal channels (420). Reprocessing system (410) ceases operation of detergent pump (416) when the elapsed flow time equals a predetermined time threshold for detergent delivery. Subsequently, at step (486), reprocessing system (410) initiates water pump (426) to deliver water to endoscope (400) via flush lines (444) and through internal channels (420), to thereby rinse any remaining detergent (86) out from internal channels (420) and into basin (14a). In this instance, flow sensor (427) measures an elapsed duration of flow as water pump (426) actively pumps water toward internal channels (420). Reprocessing system (410) ceases operation of water pump (426) when the elapsed flow time equals a predetermined time threshold for rinsing. In other examples, reprocessing system (410) may control pumps (416, 426) and/or flush valves (446) to cease the flow of detergent and water to internal channels (420) when the respective flow sensor (417, 427) observes a predetermined flow rate of the respective fluid.

At step (488), reprocessing system (410) initiates air pump (422) to send pressurized air from air supply system (421) through filter (423) and into endoscope (400). The stream of air passes through internal channels (420) thereby purging internal channels (420) of any residual detergent (86) or water contained therein. Air pump (422) continues to flow pressurized air through internal channels (420) until a specified flow duration elapses, signaling for reprocessing system (410) to cease operation of air pump (422). Reprocessing system (410) terminates air pump (422) once the elapsed flow time has reached a predetermined time threshold for air purging. At step (490), with air pump (422) inactive, disinfectant pump (412) beings to pump high concentrate disinfectant (92) to internal channels (420) of endoscope (400) simultaneously.

Reprocessing system (410) monitors the volume of disinfectant (92) transferred from disinfectant storage (411) to endoscope (400) and ceases operation of disinfectant pump (412) when the volume delivered substantially equals a predetermined threshold, as seen at step (492). Reprocessing system (410) closes all flush valves (446) simultaneously with the deactivation of disinfectant pump (412). In this instance, as seen at step (494), reprocessing system (410) evaluates whether internal channels (420) of endoscope (400) have stored the high concentrate disinfectant (92) for a minimum dwell time. As merely an illustrative example, the predetermined dwell time can range between approximately 10 seconds to 30 seconds. Although not shown, it should be understood that in some versions reprocessing system (410) may forego holding the high concentrate disinfectant (92) in the internal channels (420) for the minimum dwell time. Instead, flush valves (446) may remain open after the deactivation of disinfectant pump (412) and reprocessing system (410) may initiate water pump (526) and air pump (422), respectively in sequential order as described above.

At step (496), once reprocessing system (410) has determined that internal channels (420) have maintained disinfectant (92) for the minimum dwell time, flush valves (446) are reopened and air pump (422) is reactivated. In this instance, pressurized air is flowed through internal channels (420) to thereby purge disinfectant (92) from endoscope (400). In other versions, water may be directed through internal channels (420) to purge disinfectant (92). The flow rate of disinfectant (92) being released from within internal channels (420) into basin (14a) is increased due to the flow of pressurized air (or water), thereby enhancing the bioburden removal. At step (497), with disinfectant (92) released into basin (14a) and contained therein, reprocessing system (410) determines whether the above described fill and purge process defining a disinfection cycle has been performed a predetermined "n" number of times. By way of example only, the predetermined "n" number of times may be two times, three times, four times, five times, six times, or more times. For instance, in some versions "n" times may be in the range of 16 times to 33 times, or more. Upon the determination by reprocessing system (410) that additional fill and purge disinfection cycles remain to be completed, reprocessing system (410) transfers the previously used disinfectant (92) from basin (14a) to water pump (426) for subsequent use in the next cycle, as seen in step (498).

In this instance, reprocessing system (410) will continue to perform step (490) through step (497) until reprocessing system (410) determines that no additional disinfection cycles remain to be completed. In other words, reprocessing method (480) will proceed to step (499) to terminate the disinfection stage when reprocessing system (410) has performed the fill and purge disinfection cycle the predetermined "n" number of times.

While the disinfection stage of reprocessing method (480) is shown and described above as being repeatable for a predetermined number "n" of disinfection cycles (i.e., a type of fill and purge cycle, as described above), each comprising step (490) through step (497), it will be appreciated that other stages of reprocessing method (480) may be repeated for a respective, predetermined number of fill and purge cycles as well. For instance, the washing and rising stage of method (480) defined by step (482) through step (486) may be repeated for a respective predetermined number of cycles, each being a fill and purge cycle.

B. Medical Device Reprocessing Apparatus and Method Using Concentrated Disinfectant As previously mentioned, in some instances an endoscope (200) may include an elevator channel with a cable or wire positioned therein, such as in a duodenoscope. The cable contained within an elevator channel of a duodenoscope may be in the form of a twisted cable having various gaps and crevices capable of housing bioburdens, water, particles, and other substances therebetween. Further, due to the surface tension of the twisted cable or wire, water and other particles may remain in the gaps and crevices even after a disinfectant is delivered into the elevator channel. The remaining water or other substances contained within the elevator channel may tend to dilute any disinfectant subsequently delivered into the elevator channel for disinfection, thereby rendering the process of reducing the bioburden level of the internal channels more difficult. Additionally, the presence of the cable or wire within the elevator channel creates an additional restriction as the cable or wire significantly limits the volume of disinfectant that can flow through the elevator channel.

Ultimately, with an elevator channel having a small diameter and the presence of a cable or wire contained therein, the challenge to reduce the bioburden level in the endoscope (200) significantly increases. Providing a reprocessing system and method similar to reprocessing system (410) and reprocessing method (480) described above, may be desirable to adequately disinfect the internal channels of an endoscope through a recurring cleaning cycle. However, with the enhanced difficulties in reprocessing elevator channels containing a cable or wire contained therein, it may be desirable for the reprocessing system and method to utilize disinfectant concentrate during each cycle. In this instance, previously used disinfectant is not recycled through the reprocessing system to ensure the concentration of the disinfectant is relatively high for each recurring cycle to sufficiently increase the bioburden reduction efficacy in the elevator channel of a duodenoscope.

Providing a methodical approach to disinfecting the inner components of an endoscope may be beneficial to ensure the proper degree of bioburden reduction is achieved in each instance. The following description provides various examples of a reprocessing system and method configured to adequately disinfect the internal channels of an endoscope (200) through a recurring cleaning cycle using concentrated disinfectant for each cycle. It should be understood that the reprocessing method described below may be readily incorporated into any of the various reprocessing systems (2, 310, 310', 410) and to any of the various endoscopes (200) described above. Other suitable ways in which the below-described reprocessing method may be used will be apparent to those of ordinary skill in the art in view of the teachings herein.

Figure 8:
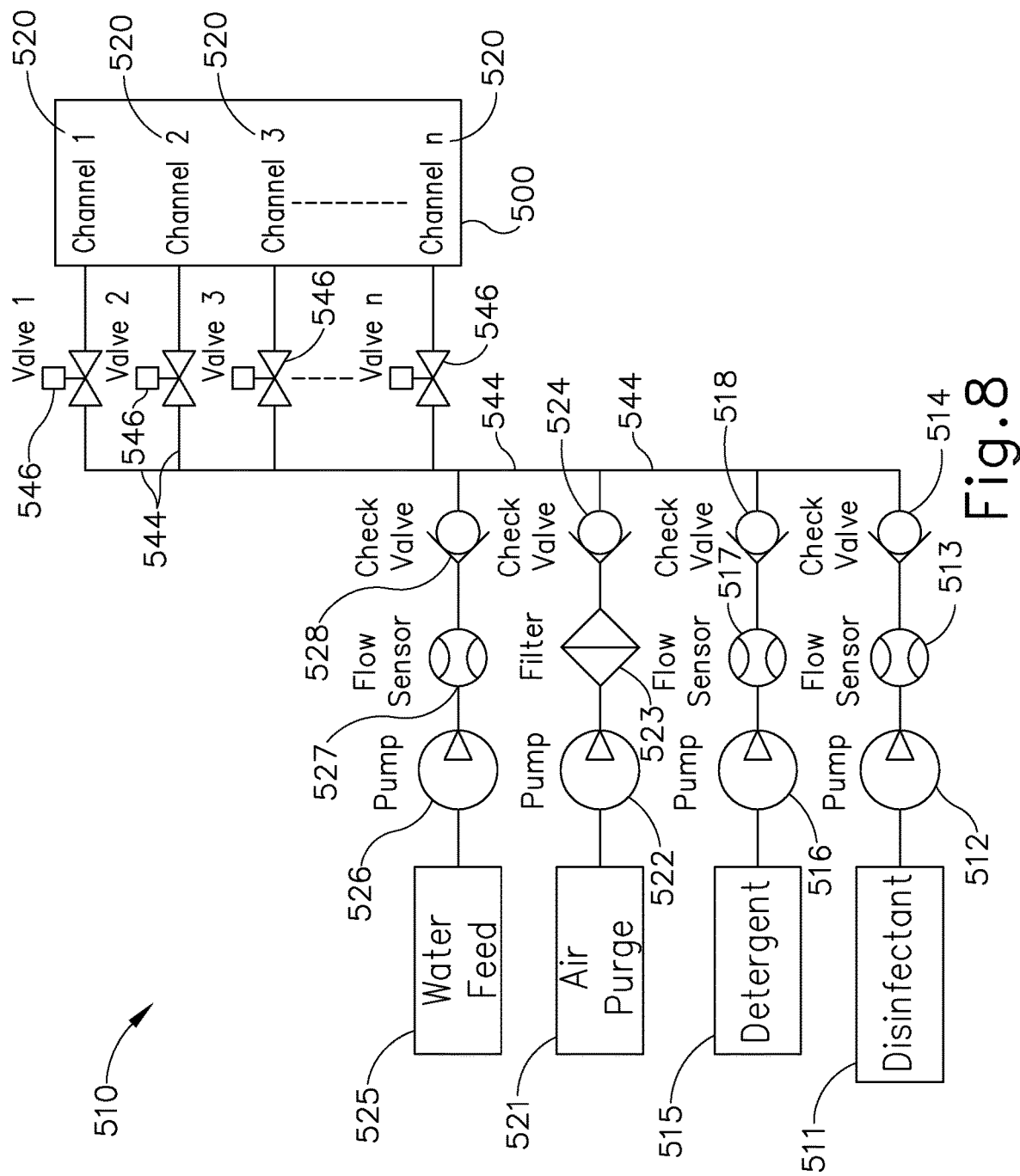
FIG. 8 depicts a partial schematic diagram of an exemplary variation of the reprocessing system of FIG. 1.

FIG. 8 shows a block schematic of an exemplary reprocessing system (510) including a disinfectant storage (511), a detergent storage (515), an air supply system (521), and a water supply (525). Except as otherwise described below, reprocessing system (510), disinfectant storage (511), detergent storage (515), air supply system (521), and water reservoir (525) are configured and operable just like reprocessing system (2, 310, 310', 410), disinfectant storage (92, 360, 411), disinfectant storage (86, 415), air supply system (36, 421), and water supply (50, 425), respectively, described above. Internal channels (520) of an endoscope (500) are in fluid communication with disinfectant storage (411), detergent storage (515), air supply system (521) and water reservoir (525) via flush lines (544). Reprocessing system (510) is operable to deliver disinfectant solution (92), detergent solution (86), air and water to internal channels (520) of endoscope (500) individually and sequentially. While only one endoscope (500) is shown as being reprocessed in reprocessing system (510), it should be understood that reprocessing system (510) may be capable of reprocessing more than one endoscope (500) simultaneously and/or in a sequence.

Flush lines (544) include a flush valve (546) for each channel (520) operatively connected to reprocessing system (510). Flush valves (546) are positioned downstream of disinfectant storage (511), detergent storage (515), air supply system (521), and water reservoir (525). In the present example, disinfectant storage (511) is in fluid communication with a disinfectant pump (512), a flow sensor (513) and a check valve (514) in sequence, such that disinfectant pump (512) is configured to transfer disinfectant (92) from disinfectant storage (511) to flow sensor (513) and through check valve (514) via flush lines (544). In this instance, disinfectant solution (92) is a high concentrate disinfectant or sterilant that is capable of providing adequate bioburden reduction within internal channels (520).

Flow sensor (513) is operable to monitor the flow of concentrated disinfectant (92) delivered from disinfectant pump (512) to internal channels (520) of endoscopes (500). Control system (20) of reprocessing system (510) is configured to execute a control algorithm (see FIG. 9) to open flush valve (546), which is in fluid connection with endoscope (500), and retrieve the data monitored by flow sensor (513). Control system (20) is operable to terminate fluid communication between disinfectant pump (512) and endoscope (500) when the data indicates that internal channels (520) have received a sufficient amount of disinfectant (92) by closing flush valves (546).

Similarly, detergent storage (515) is in fluid communication with a detergent pump (516), a flow sensor (517) and a check valve (518) in sequence, such that detergent pump (516) is configured to transfer detergent solution (86) to flow sensor (517) and through check valve (518) via flush lines (544). Flow sensor (517) is operable to monitor the elapsed duration as detergent (86) is delivered from detergent pump (516) to internal channels (520) of endoscope (500). In other words, reprocessing system (510) is configured to terminate the fluid communication between detergent pump (516) and flush valves (546), by closing flush valves (546), once the elapsed duration monitored by flow sensor (517) has met a predetermined time threshold for delivering detergent (86) to endoscope (500). Alternatively, or in conjunction, reprocessing system (510) is configured to cease operation of detergent pump (516) from pumping detergent (86) to internal channels (520). In each instance, reprocessing system (510) is configured to close flush valves (546) when internal channels (520) have received a sufficient amount of detergent (86) therein, as sensed by flow sensor (517).

Air supply system (521) is in communication with an air pump (522), a filter (523) and a check valve (524). Air pump (522) is configured to push pressurized air from air supply system (521) through filter (523) and check valve (524), thereby delivering a stream of air into and through internal channels (520) of endoscope (500). Filter (523) is operable to filter and remove microbes from the incoming air stream extracted from air supply system (521). In some illustrative examples, filter (523) comprises a HEPA microbe-removing filter. In some versions, reprocessing system (510) may exclude filter (523) in communication with air pump (522) and check valve (524). Water reservoir (525) is in fluid communication with a water pump (526), a flow sensor (527) and a check valve (528). Water pump (526) is configured to pump water from water reservoir (525) to flow sensor (527) and through check valve (528) via flush lines (544).

Reprocessing system (510) is operable to open flush valve (546) and to measure the quantity of water delivered from water pump (526) to internal channels (520) of endoscope (500). Flow sensor (527) is operable to monitor the quantity of water delivered to internal channels (520). In this instance, reprocessing system (510) is configured to close flush valve (546) when internal channels (520) have received a sufficient amount of water. Reprocessing system (510) further includes basin (14a) in fluid communication with internal channels (520) of endoscope (500) via flush lines (544). Basin (14a) is operable to receive any fluids or air released from internal channels (520). As previously mentioned, although not shown, it should be understood that reprocessing system (510) may include a single pump assembly such that the same pump is configured to deliver detergent (86), water, pressurized air, and concentrated detergent (92). In this instance, reprocessing system (510) is configured to selectively open and close a series of flush valves (546) to individually deliver the various substances with the single pump assembly.

Figure 9:
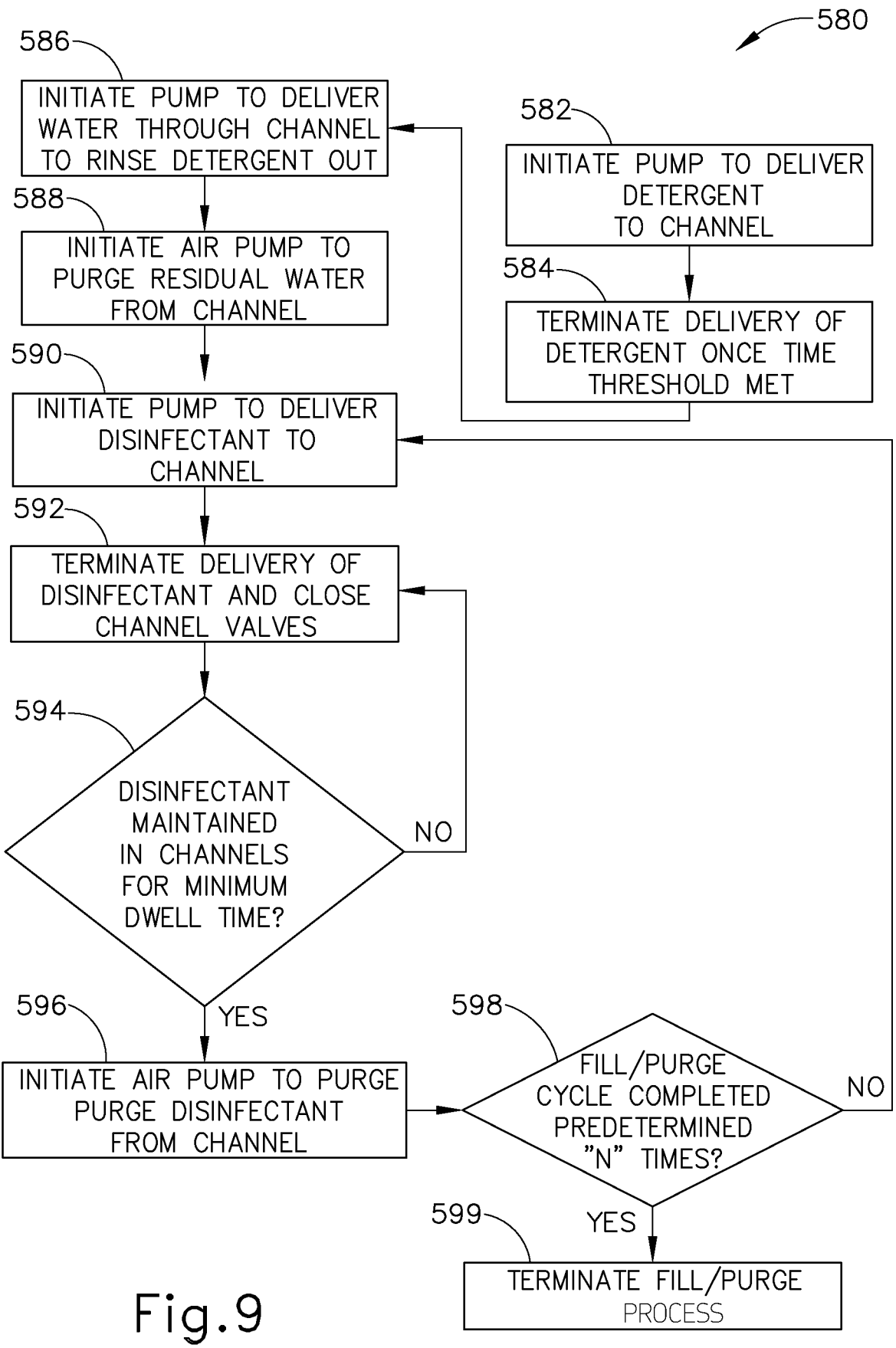
FIG. 9 depicts a flow diagram illustrating another exemplary reprocessing method utilized by the reprocessing system of FIG. 8, with the internal channels of an endoscope undergoing a repetitive disinfecting cycle.

FIG. 9 shows a flow diagram illustrating steps of an exemplary reprocessing method (580) that may be used by reprocessing system (510) to perform a predetermined number of fill and purge disinfection cycles of internal channels (520) of endoscope (500). At step (582), reprocessing system (510) initiates detergent pump (512) to deliver detergent solution (86) to endoscope (500) via flush lines (544). Reprocessing system (510) is configured to deliver detergent (86) through internal channels (520) at a predetermined flow rate. At step (584), as detergent (86) is transferred from detergent storage (515) to endoscope (500), flow sensor (517) measures an elapsed duration of flow as detergent pump (516) actively pumps detergent (86) toward internal channels (520). Reprocessing system (510) ceases operation of detergent pump (516) when the elapsed flow time equals a predetermined time threshold for detergent delivery. Subsequently, at step (586), reprocessing system (510) initiates water pump (526) to deliver water to endoscope (500) via flush lines (544) and through internal channels (520), to thereby rinse any remaining detergent (86) out from internal channels (520) and into basin (14*a*). In this instance, flow sensor (527) measures an elapsed duration of flow as water pump (526) pumps water into internal channel (520). Reprocessing system (510) ceases operation of water pump (526) when the elapsed flow time equals a predetermined time threshold for rinsing.

At step (588), reprocessing system (510) initiates air pump (522) to send pressurized air from air supply system (521) through filter (523) and into endoscope (500). The stream of air passes through internal channels (520) thereby purging internal channels (520) of any residual detergent (86) or water contained therein. Air pump (522) continues to flow pressurized air through internal channels (520) until a specified flow duration elapses signaling for reprocessing system (510) to cease operation of air pump (522). Reprocessing system (510) terminates air pump (522) once the elapsed flow time has reached a predetermined time threshold for air purging. At step (590), with air pump (522) inactive, disinfectant pump (512) beings to pump high concentrate disinfectant (92) to internal channels (520) of endoscope (500) simultaneously. Reprocessing system (510) monitors the volume of disinfectant (92) transferred from disinfectant storage (511) to endoscopes (500) and ceases operation of disinfectant pump (512) when the volume delivered substantially equals a predetermined threshold, as seen at step (592). Reprocessing system (510) closes all flush valves (546) simultaneous with the deactivation of disinfectant pump (512). In this instance, as seen at step (594), reprocessing system (510) evaluates whether internal channels (520) of endoscope (500) has stored the high concentrate disinfectant (92) for a minimum dwell time. As merely an illustrative example, the predetermined dwell time can range between approximately 10 seconds to 30 seconds. Although not shown, it should be understood that in some versions reprocessing system (510) may forego holding the high concentrate disinfectant (92) in the internal channels (520) for the minimum dwell time. Instead, flush valves (546) may remain open after the deactivation of disinfectant pump (512) and reprocessing system (510) may initiate water pump (526) and air pump (522), respectively in sequential order as described above.

At step (596), once reprocessing system (510) has determined that internal channels (520) have maintained disinfectant (92) for the minimum dwell time, flush valves (546) are reopened and air pump (522) is reactivated. In this instance, pressurized air is flowed through internal channels (520) to thereby purge disinfectant (92) from endoscope (500). The flow rate of disinfectant (92) being released from within internal channels (520) into basin (14*a*) is increased due to the flow of pressurized air, thereby enhancing the bioburden removal. At step (598), with disinfectant (92) released into basin (14*a*) and contained therein, reprocessing system (510) determines whether the above described fill and purge disinfection cycle has been performed a predetermined "n" number of times. Upon the determination by reprocessing system (510) that additional fill and purge disinfection cycles remain to be completed, reprocessing system (510) will continue to perform step (590) through step (598) until reprocessing system (510) determines that no additional fill and purge disinfection cycles remain to be completed. In other words, reprocessing method (580) will proceed to step (599) to terminate the disinfection state when reprocessing system (510) has performed the fill and purge disinfection cycle the predetermined "n" number of times.

V. Exemplary Methods of Filing and Purging Internal Channels of a Medical Device Based on Sensor Feedback As described above, forcibly directing various liquids such as detergents and disinfectants through the internal channels of a medical device is generally effective to lower the bioburden level within the channels. In particular, the liquids exert shear stresses on the inner walls of the channels that have destructive effects on local bioburden. When liquid enters an empty channel, the liquid flow rate of the liquid is high, and the associated shear stress exerted on the channel walls by the liquid is proportionally high. As the channel approaches a filled state, backpressure within the channel increases and causes the liquid flow rate and the associated shear stress to decrease. When water or pressurized air is injected into the filled channel to purge the liquid, the liquid flow rate and associated shear stress increases as the volume of the liquid within the channel decreases. Thus, to maximize shear stress and resulting bioburden reduction within a channel during reprocessing retreatment, it may be desirable to complete each fill and purge cycle as quickly as possible. The exemplary elements and methods described below promote optimal bioburden reduction efficacy within the internal channels of a medical device by controlling filling and purging of the channels to maximize shear stresses exerted on the channel walls.

Figure 10:
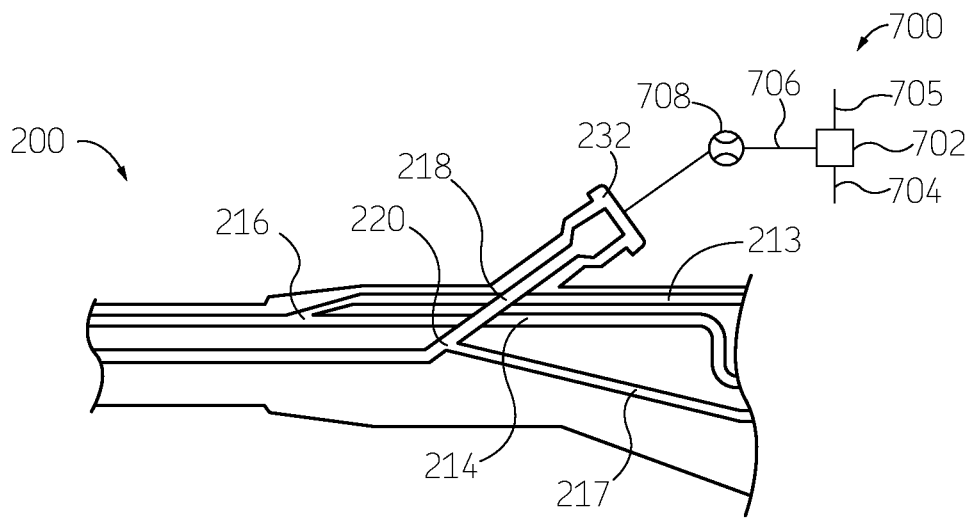
FIG. 10 depicts an enlarged cross-sectional side view of a proximal portion of the endoscope of FIG. 3, schematically showing an internal channel of the endoscope fluidly connected with a respective flush line of another exemplary reprocessing system, the flush line having a flush valve and a flow rate sensor.

A. Filling and Purging Internal Channels of Device Based on Feedback from Flow Rate Sensor FIG. 10 shows a proximal portion of endoscope (200) connected to a portion of another exemplary reprocessing system (700). Reprocessing system (700) is similar to reprocessing systems (2, 310, 410, 510) described above except as otherwise described below. Reprocessing system (700) of the present example includes a multi-way flush valve unit (702) that may be in the form of a three-way valve or a pair of two-way valves, for example as described below in connection with reprocessing systems (1000, 1100) of FIGS. 15 and 16. A first inlet of flush valve unit (702) is coupled to a liquid fill line (704), a second inlet of flush valve unit (702) is coupled to an air purge line (705), and an outlet of flush valve unit (702) is coupled to a flush line (706). While flush line (706) is shown fluidly coupled with biopsy channel (218) via connection (232) in the present example, it will be appreciated that flush line (706) may be fluidly coupled with various other internal channels (210, 212, 213, 214, 217) of endoscope (200) in other examples. Furthermore, reprocessing system (700) may include a plurality of flush lines (706) and respective multi-way flush valve units (702), each being configured to fluidly couple with a respective internal channel (210, 212, 213, 214, 217, 218) of endoscope (200).

Liquid fill line (704) of reprocessing system (700) is configured to deliver a fill liquid, such as detergent or disinfectant, to flush valve unit (702), which is operable to then direct the fill liquid to internal channel (210, 212, 213, 214, 217, 218) via flush line (706). Air purge line (705) is configured to deliver compressed air to flush valve unit (702), which is operable to then direct the compressed air to internal channel (210, 212, 213, 214, 217, 218) via flush line (706). In some versions, flush valve unit (702) may include a third inlet coupled to a liquid rinse line (not shown) configured to deliver a liquid, such as water, to flush valve unit (702), which would then direct the liquid through flush line (706) for rinsing internal channel (210, 212, 213, 214, 217, 218).

Flush valve unit (702) is similar to flush valves (446) described above in that flush valve unit (702) is selectively operable by a controller (not shown), which may be similar to controller (20) of system (2), to direct fluids from the various fluid sources (not shown) of reprocessing system (700) to an internal channel (210, 212, 213, 214, 217, 218) of endoscope (200). For instance, the controller may selectively operate flush valve unit (702) to direct one or more liquids such as detergent, water, or disinfectant through flush line (706) and into internal channel (210, 212, 213, 214, 217, 218). The controller may further operate flush valve (702) to direct compressed air from air purge line (705), through flush line (706), and into internal channel (210, 212, 213, 214, 217, 218). Accordingly, "fluid" as used herein encompasses both liquids and gasses.

As shown in FIG. 10, reprocessing system (700) further includes a flow rate sensor (708) coupled with flush line (706) downstream of flush valve unit (702). Flow rate sensor (708) may be arranged directly within flush line (706), or otherwise in fluid communication with flush line (706). In other versions, flow rate sensor (708) may be coupled with liquid fill line (704) upstream of flush valve unit (702). Such a configuration may be desirable in some instances to avoid exposing flow rate sensor (708) to compressed air directed through flush line (706) from air purge line (705). As described in greater detail below, flow rate sensor (708) is operable to measure a flow rate of a liquid being directed into internal channel (210, 212, 213, 214, 217, 218), and communicate the measured flow rate to the system controller.

Figure 13:
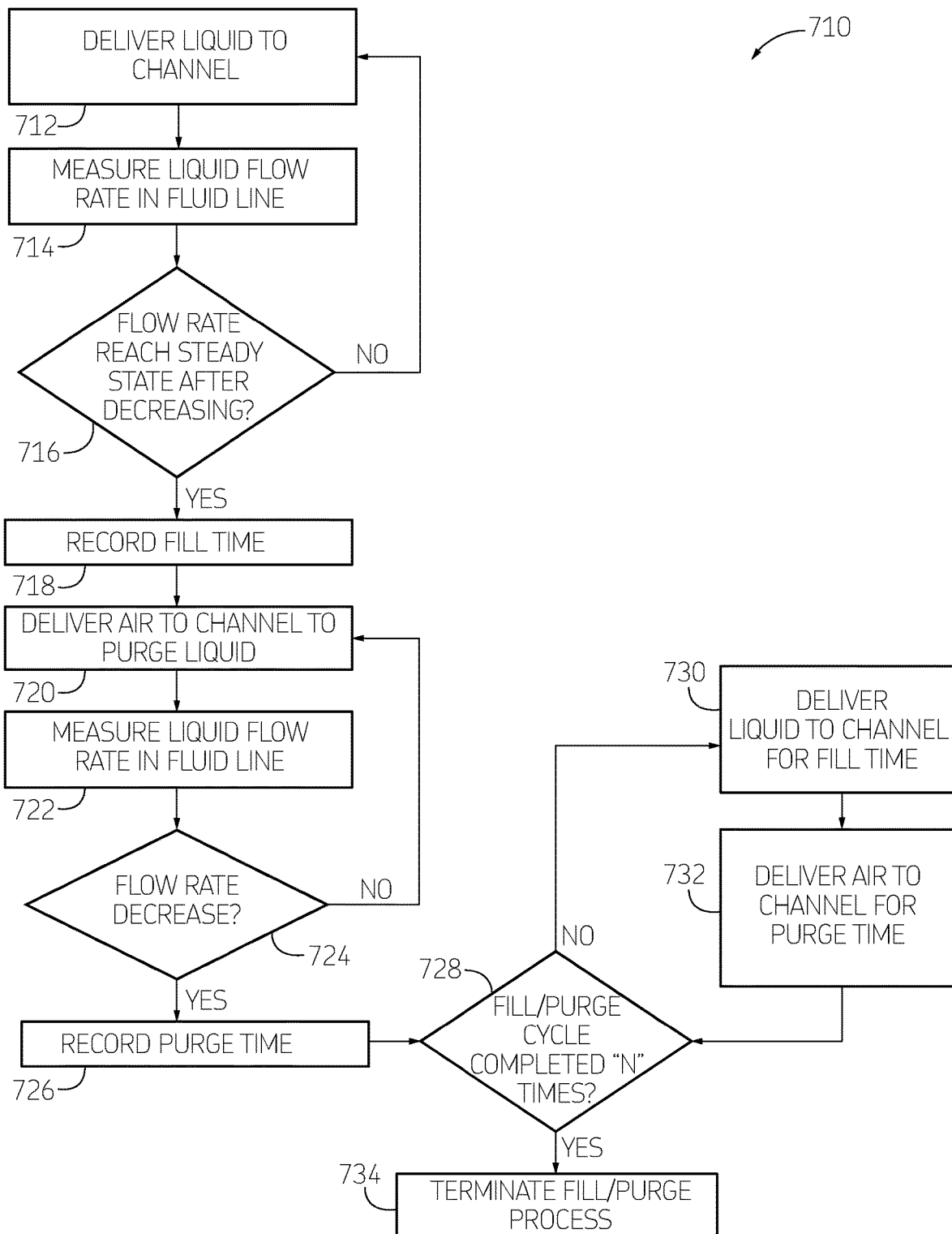
FIG. 13 depicts a flow diagram illustrating an exemplary method for filling and purging an internal channel of an endoscope with the exemplary reprocessing system of FIG. 10 based on fluid flow rates measured by the flow rate sensor.

FIG. 13 shows a flow diagram illustrating steps of an exemplary method (710) for using reprocessing system (700) described above to reprocess an internal channel of a medical device, such as any one or more of internal channels (210, 212, 213, 214, 217, 218) of endoscope (200). As described below, liquid flow rate data provided by flow rate sensor (708) is referenced by the system controller to automatically determine an optimum fill time and an optimum purge time for the respective internal channel (210, 212, 213, 214, 217, 218) so as to maximize shear stress and resulting bioburden reduction efficacy within the channel (210, 212, 213, 214, 217, 218) during a fill a purge cycle.

In versions of reprocessing system (700) that include multiple flush lines (702) each having a respective flow rate sensor (708), flow rate sensors (708) may communicate with the system controller independently such that the controller may automatically determine an optimum fill time and purge time for each of the respective internal channels (210, 212, 213, 214, 217, 218). This may be particularly advantageous for applications in which internal channels (210, 212, 213, 214, 217, 218) are formed with different diameters such that channels (210, 212, 213, 214, 217, 218) accept different volumes of liquids during the fill step of a fill and purge cycle.

As shown in FIG. 13, method (710) includes an initial step (712) of activating a liquid pump of reprocessing system (700) and actuating flush valve unit (702) to deliver a liquid to through flush line (706) and into internal channel (210, 212, 213, 214, 217, 218). The liquid may be in the form of water, detergent, disinfectant/sterilant, or various other suitable reprocessing liquids readily apparent to those of ordinary skill in the art in view of the teachings herein. Additionally, the liquid pump may be similar to any of the liquid pumps of reprocessing systems (2, 310, 410, 510, 610) described above. At step (714), the reprocessing system controller begins monitoring the liquid flow rate of the liquid as it passes through flush line (706), or another fluid line with which flow rate sensor (708) is coupled, via measurements provided by flow rate sensor (708). Throughout the channel filing process, the controller assesses at step (716) whether the measured liquid flow rate within flush line (706) has decreased to the point of stabilizing at a steady state, thereby indicating that internal channel (210, 212, 213, 214, 217, 218) has completely filled with liquid. Specifically, the controller compares the measured flow rate detected by flow rate sensor (708) to a predetermined flow rate associated with the liquid and channel (210, 212, 213, 214, 217, 218) in a filled state.

It will be appreciated that the flow rate measured within flush line (706) by flow rate sensor (708) may start at a first flow rate and decrease as channel (210, 212, 213, 214, 217, 218) fills with liquid. When the channel (210, 212, 213, 214, 217, 218) has filled, the flow rate within flush line (706) stabilizes at a decreased second flow rate. For instance, in one example the liquid flow rate may start at approximately 100 mL per minute upon initial entry of liquid into internal channel (210, 212, 213, 214, 217, 218) when the flush valve unit (702) is initially actuated, and then settle at a steady state flow rate of approximately 50 mL per minute after approximately 2 seconds of fill time measured from the actuation of flush valve unit (702). If the controller determines that the liquid flow rate has not yet reached a steady state flow, thus indicating that internal channel (210, 212, 213, 214, 217, 218) has not yet completely filled with liquid, the controller continues to power the liquid pump to deliver liquid to internal channel (210, 212, 213, 214, 217, 218) by repeating steps (712)-(716). Once the controller identifies at step (716) that the liquid within internal channel (210, 212, 213, 214, 217, 218) has reached a steady state flow, the controller determines that internal channel (210, 212, 213, 214, 217, 218) has completely filled. At step (718), the controller records the amount of time that the liquid pump has been running since the initial actuation of flush valve unit (702) to fill channel (210, 212, 213, 214, 217, 218) with liquid ("Fill Time"). Simultaneously, the controller may actuate flush valve unit (702), and optionally deactivate the liquid pump, to cease channel filling and commence channel purging, as described below.

The system controller initiates purging of channel (210, 212, 213, 214, 217, 218) at step (720) by activating an air pump, which may be similar to any of the air pumps of reprocessing systems (2, 310, 410, 510, 610) described above, and actuating flush valve unit (702) to deliver pressurized air through flush line (706) and into internal channel (210, 212, 213, 214, 217, 218). Meanwhile, the system controller continues to monitor the liquid flow rate within flush line (706) at step (722) via measurements provided by flow rate sensor (708). Upon detecting at step (724) that the measured liquid flow rate has decreased relative to a starting liquid flow rate measured at the initiation of purging step (720) (e.g., the steady state flow rate discussed above), the controller determines that the purging of channel (210, 212, 213, 214, 217, 218) is complete. In that regard, those skilled in the art will appreciate that the pressurized air passing through flush line (706) is much less dense than the liquid, such that flow rate sensor (708) will register a drop in liquid flow rate when channel (210, 212, 213, 214, 217, 218) is purged to the point that predominantly only air is passing by flow rate sensor (708) within flush line (706). In some versions, the controller may determine that purging of channel (210, 212, 213, 214, 217, 218) is complete once the measured flow rate is less than or equal to a predetermined flow rate that corresponds to an adequately purged state of channel (210, 212, 213, 214, 217, 218). Upon determining that internal channel (210, 212, 213, 214, 217, 218) has been adequately purged of liquid, the system controller ceases purging by actuating flush valve unit (702) and optionally deactivating the air pump. Simultaneously, the controller proceeds to step (726) to record the amount of time that the air pump ran since flush valve unit (702) was actuated to initiate purging of channel (210, 212, 213, 214, 217, 218) with pressurized air ("Purge Time").

At step (728), the controller assesses whether a predetermined quantity ("n") of fill and purge cycles of internal channel (210, 212, 213, 214, 217, 218) has been completed. If the predetermined quantity has not been completed, the system (700) proceeds to step (730) and actuates flush valve unit (702), and optionally also reactivates the liquid pump if previously deactivated, to deliver liquid through flush line (706) and to channel (210, 212, 213, 214, 217, 218) for the Fill Time. Immediately upon expiration of the Fill Time in step (730), the controller actuates flush valve unit (702) to cease liquid fill and commence pressurized air purge of internal channel (210, 212, 213, 214, 217, 218) at step (732). This step may optionally include deactivating the liquid pump and reactivating the air pump in some instances. During step (732), system (700) directs pressurized air into internal channel (210, 212, 213, 214, 217, 218) for the Purge Time to purge the liquid from channel (210, 212, 213, 214, 217, 218). In some versions, system (700) may instead direct pressurized air into channel (210, 212, 213, 214, 217, 218) for the Fill Time.

Immediately upon completing step (732), or while completing step (732), the controller repeats step (728) to determine whether the predetermined quantity of fill and purge cycles has been completed. If the predetermined quantity has still not yet been completed, the controller repeats steps (730), (732), and (728) sequentially as many times as necessary until the predetermined quantity of cycles is completed. Then, the controller proceeds to step (734) and terminates the filling and purging process.

As described above, method (710) may be performed independently for each of the internal channels of a medical device, such as each of internal channels (210, 212, 213, 214, 217, 218) of endoscope (200).

Figure 11:
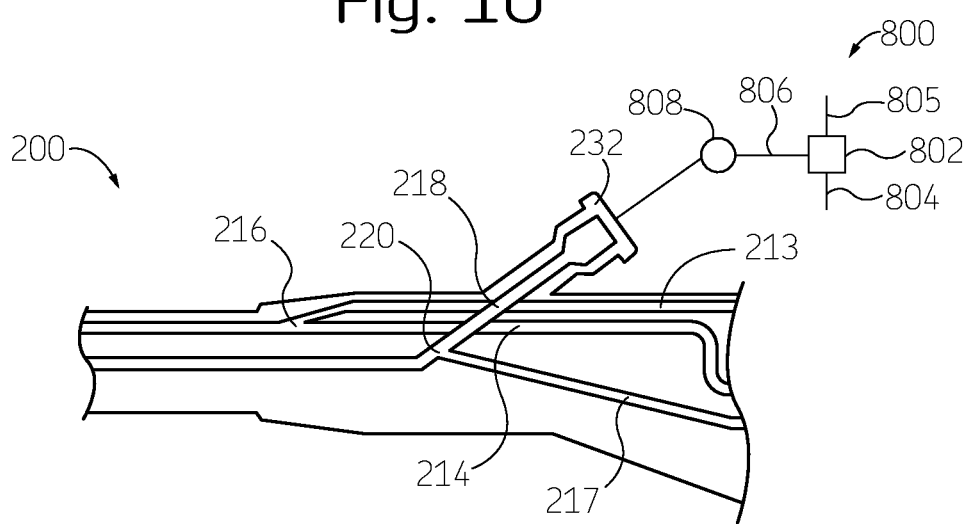
FIG. 11 depicts an enlarged cross-sectional side view of a proximal portion of the endoscope of FIG. 3, schematically showing an internal channel of the endoscope fluidly connected with a respective flush line of another exemplary reprocessing system, the flush line having a flush valve and a pressure sensor.

B. Filling and Purging Internal Channels of Device Based on Feedback from Pressure Sensor FIG. 11 shows a proximal portion of endoscope (200) connected to a portion of another exemplary reprocessing system (800). Reprocessing system (800) is similar to reprocessing system (700) described above except as otherwise described below. Like reprocessing system (700), reprocessing system (800) includes a multi-way flush valve unit (802) having a first inlet coupled to a liquid fill line (804), a second inlet coupled to an air purge line (705), and an outlet coupled to a flush line (806). While flush line (806) is shown fluidly coupled with biopsy channel (218) via connection (232) in the present example, it will be appreciated that flush line (806) may be fluidly coupled with various other internal channels (210, 212, 213, 214, 217) of endoscope (200) in other examples. Furthermore, reprocessing system (800) may include a plurality of flush lines (806) and respective multi-way flush valve units (802), each being configured to fluidly couple with a respective internal channel (210, 212, 213, 214, 217, 218) of endoscope (200).

Reprocessing system (800) includes a pressure sensor (808) in place of flow rate sensor (708) of reprocessing system (700). In the present version, pressure sensor (808) is coupled with flush line (806) downstream of flush valve unit (802). In other versions, pressure sensor (808) may be coupled with liquid fill line (804) upstream of flush valve unit (802). As described in greater detail below, pressure sensor (808) is operable to measure a pressure within flush line (806) during operation of reprocessing system (800) and communicate the measured pressure to a controller of system (800).

Figure 14:
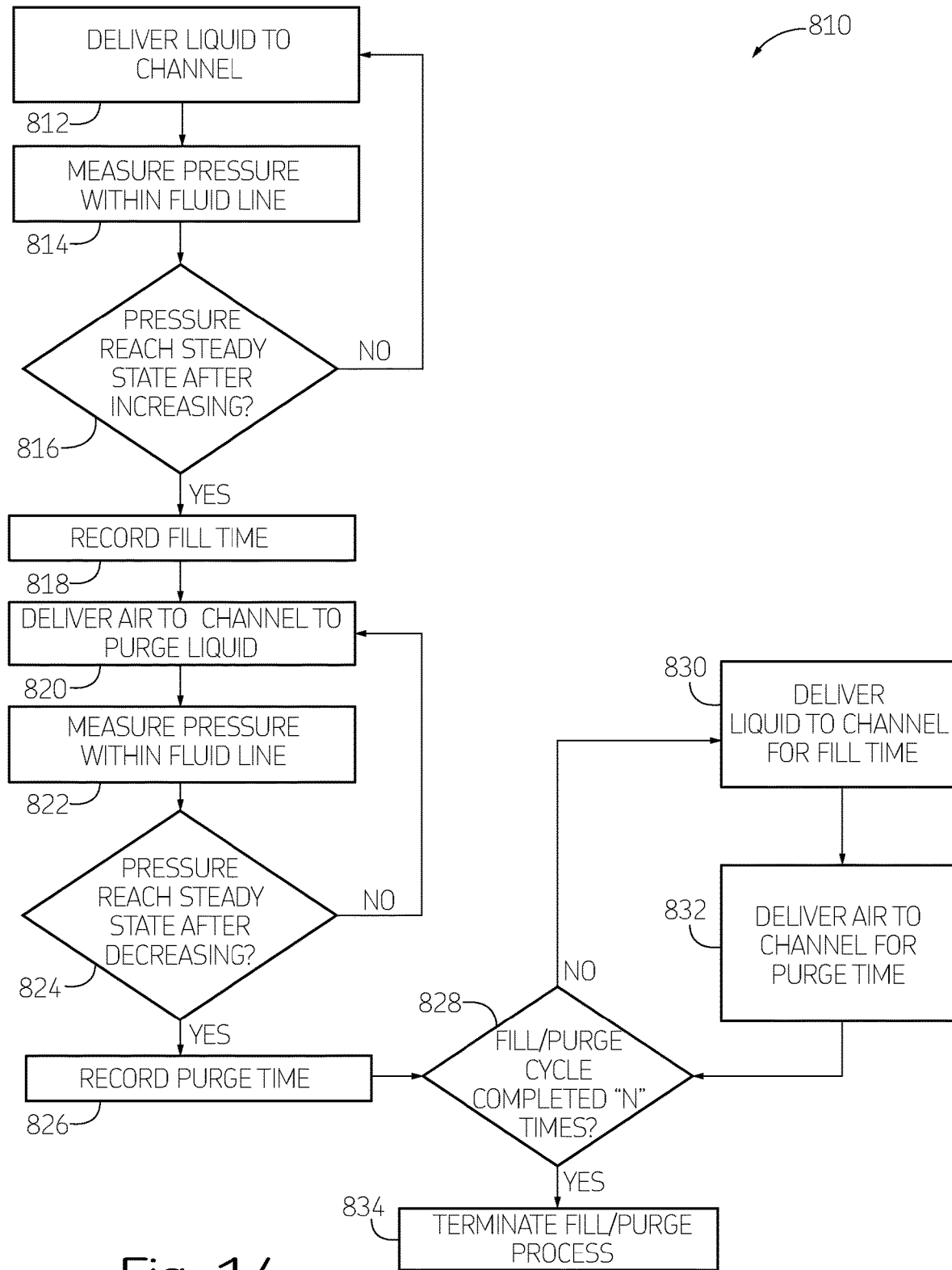
FIG. 14 depicts a flow diagram illustrating an exemplary method for filling and purging an internal channel of an endoscope with the exemplary reprocessing system of FIG. 11 based on fluid pressures measured by the pressure sensor.

FIG. 14 shows a flow diagram illustrating steps of an exemplary method (810) for using reprocessing system (800) described above to reprocess an internal channel of a medical device, such as any one or more of internal channels (210, 212, 213, 214, 217, 218) of endoscope (200). As described below, pressure data provided by pressure sensor (808) is referenced by the system controller to automatically determine an optimum fill time and an optimum purge time for the respective internal channel (210, 212, 213, 214, 217, 218) so as to maximize shear stress and resulting bioburden reduction efficacy within the channel (210, 212, 213, 214, 217, 218) during a fill a purge cycle.

In versions of reprocessing system (800) that include multiple flush lines (802) each having a respective flow rate sensor (808), flow rate sensors (808) may communicate with the system controller independently such that the controller may automatically determine an optimum fill time and purge time for each of the respective internal channels (210, 212, 213, 214, 217, 218). This may be particularly advantageous for applications in which internal channels (210, 212, 213, 214, 217, 218) are formed with different diameters such that channels (210, 212, 213, 214, 217, 218) accept different volumes of liquids during the fill step of a fill and purge cycle.

As shown in FIG. 14, method (810) includes an initial step (812) of activating a liquid pump of reprocessing system (800) and actuating flush valve unit (802) to deliver a liquid through flush line (806) and into internal channel (210, 212, 213, 214, 217, 218). The liquid may be in the form of water, detergent, disinfectant/sterilant, or various other suitable reprocessing liquids readily apparent to those of ordinary skill in the art in view of the teachings herein. Additionally, the liquid pump may be similar to any of the liquid pumps of reprocessing systems (2, 310, 410, 510, 610) described above. At step (814), the reprocessing system controller begins monitoring the internal pressure within flush line (806), or another fluid line with which pressure sensor (808) is coupled, via measurements provided by pressure sensor (808). Throughout the channel filing process, the controller continually assesses whether the measured pressure within flush line (806) has increased to the point of stabilizing at a steady state pressure, thereby indicating that channel (210, 212, 213, 214, 217,218) has completely filled with liquid. Specifically, the controller compares the measured pressure detected by pressure sensor (808) to a predetermined pressure associated with the liquid and channel (210, 212, 213, 214, 217, 218) in a filled state.

In that regard, it will be appreciated by those skilled in the art that the pressure measured by pressure sensor (808) within flush line (806) may increase as channel (210, 212, 213, 214, 217, 218) fills, and eventually stabilize at a maximum pressure once channel (210, 212, 213, 214, 217, 218) is completely filled. If the controller determines that the pressure within flush line (806) has not yet stabilized at a maximum pressure, thus indicating that internal channel (210, 212, 213, 214, 217, 218) has not yet completely filled with liquid, the controller continues to power the liquid pump to deliver liquid to internal channel (210, 212, 213, 214, 217, 218) by repeating steps (812)-(816). Once the controller identifies that the pressure within flush line (806) has stabilized at a maximum pressure, the controller determines that internal channel (218) is completely filled. At step (818), the controller records the amount of time that the liquid pump has been running since the initial actuation of flush valve unit (802) to fill channel (210, 212, 213, 214, 217, 218) with liquid ("Fill Time"). Simultaneously, the controller may actuate flush valve unit (802), and optionally deactivate the liquid pump, to cease channel filling and commence channel purging, as described below.

The system controller initiates purging of channel (210, 212, 213, 214, 217, 218) at step (820) by activating an air pump, which may be similar to any of air pumps (38, 110, 422, 522) described above, and actuating flush valve unit (802) to deliver pressurized air through flush line (806) and into channel (210, 212, 213, 214, 217, 218). Meanwhile, the system controller continues to monitor the pressure within flush line (806) at step (822) via measurements provided by pressure sensor (808). Upon detecting at step (824) that the measured pressure has decreased and stabilized at a new pressure, the controller determines that the purging of channel (210, 212, 213, 214, 217, 218) is complete.

As described above, it will be appreciated by those skilled in the art that the pressurized air passing through channel (218) is much less dense than the liquid, such that the pressure sensor (808) will register a drop in pressure within flush line (806) when channel (210, 212, 213, 214, 217, 218) is purged to the point that no substantially no liquid remains within channel (210, 212, 213, 214, 217, 218). In some versions, the controller may determine that purging of channel (210, 212, 213, 214, 217, 218) is complete once the measured pressure is less than or equal to a predetermined pressure that corresponds to an adequately purged state. Upon determining that internal channel (210, 212, 213, 214, 217, 218) has been adequately purged of liquid, the system controller ceases purging by actuating flush valve unit (802) and optionally deactivating the air pump. Simultaneously, the controller proceeds to step (826) to record the amount of time that the air pump ran since flush valve unit (802) was actuated to initiate purging of channel (210, 212, 213, 214, 217, 218) with pressurized air ("Purge Time").

At step (828), the controller assesses whether a predetermined quantity ("n") of fill and purge cycles of internal channel (210, 212, 213, 214, 217, 218) has been completed. If the predetermined quantity has not been completed, the system (800) proceeds to step (830) and actuates flush valve unit (802), and optionally also reactivates the liquid pump if previously deactivated, to deliver liquid through flush line (806) and to channel (210, 212, 213, 214, 217, 218) for the Fill Time. Immediately upon expiration of the Fill Time in step (830), the controller actuates flush valve unit (802) to cease liquid fill and commence pressurized air purge of internal channel (210, 212, 213, 214, 217, 218). This step may optionally include deactivating the liquid pump and reactivating the air pump in some instances. During step (832) system (800) directs pressurized air into internal channel (210, 212, 213, 214, 217, 218) for the Purge Time to purge the liquid from channel (210, 212, 213, 214, 217, 218). In some version, system (800) may instead direct pressurized air into channel (210, 212, 213, 214, 217, 218) for the Fill Time.

Immediately upon completing step (832), or while completing step (832), the controller repeats step (828) to determine whether the predetermined quantity of fill and purge cycles has been completed. If the predetermined quantity has still not yet been completed, the controller repeats steps (830), (832), and (828) sequentially as many times as necessary until the predetermined quantity ("n") of cycles is completed. Then, the controller proceeds to step (834) and terminates the filling and purging process.

As described above, method (810) may be performed independently for each of the internal channels of a medical device, such as each of internal channels (210, 212, 213, 214, 217, 218) of endoscope (200).

Figure 12:
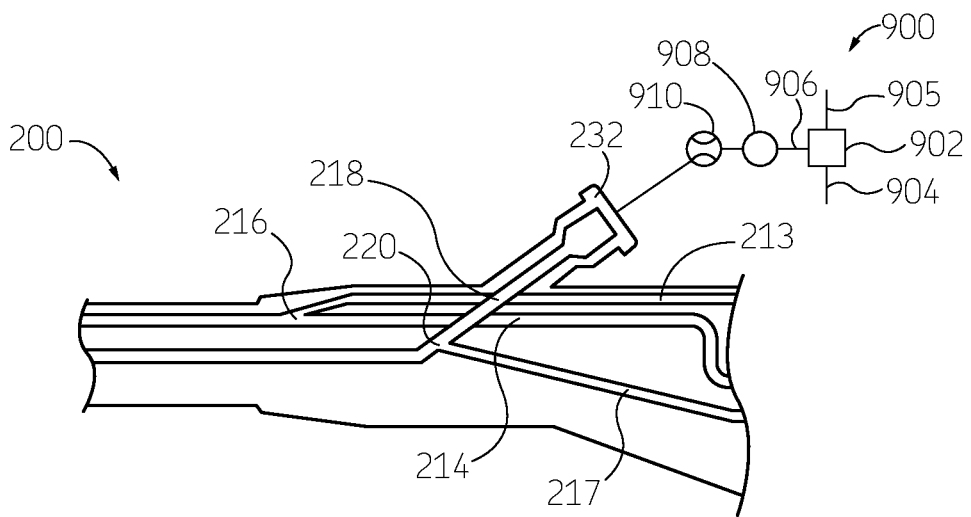
FIG. 12 depicts an enlarged cross-sectional side view of a proximal portion of the endoscope of FIG. 3, schematically showing an internal channel of the endoscope fluidly connected with a respective flush line of another exemplary reprocessing system, the flush line having a flush valve, a pressure sensor, and a flow rate sensor.

C. Filling and Purging Internal Channels of Device Based on Feedback from Flow Rate Sensor and Pressure Sensor FIG. 12 shows a proximal portion of endoscope (200) connected to a portion of another exemplary reprocessing system (900). Reprocessing system (900) is similar to reprocessing systems (700, 800) described above except as otherwise described below. Like reprocessing systems (700, 800), reprocessing system (900) of the present example includes a multi-way flush valve unit (902) having a first inlet coupled to a liquid fill line (904), a second inlet coupled to an air purge line (905), and an outlet coupled to a flush line (906). While flush line (906) is shown fluidly coupled with biopsy channel (218) via connection (232) in the present example, it will be appreciated that flush line (906) may be fluidly coupled with various other internal channels (210, 212, 213, 214, 217) of endoscope (200) in other examples. Furthermore, reprocessing system (900) may include a plurality of flush lines (906) and respective multi-way flush valve units (902), each being configured to fluidly couple with a respective internal channel (210, 212, 213, 214, 217, 218) of endoscope (200).

Reprocessing system (900) further includes a pressure sensor (908) and a flow rate sensor (910). In the present version, pressure sensor (908) and flow rate sensor (910) are coupled with flush line (906) downstream of flush valve unit (902). In other versions, flow rate sensor (910) may be coupled with liquid fill line (904) upstream of flush valve unit (902), for instance to avoid exposing flow rate sensor (910) to compressed air directed through flush line (906) from air purge line (905). Pressure sensor (908) is generally similar to pressure sensor (808) of reprocessing system (800), and flow rate sensor (910) is generally similar to flow rate sensor (708) of reprocessing system (700). In particular, pressure sensor (908) is operable to measure and communicate with a controller (not shown) of system (900) regarding a pressure within flush line (906), and flow rate sensor (910) is operable to measure and communicate with the controller regarding a flow rate of liquid passing through flush line (906).

The controller of reprocessing system (900) may monitor both sets of sensor data, provided by pressure sensor (908) and flow rate sensor (910), to automatically determine a precise Fill Time and Purge Time for a particular internal channel (210, 212, 213, 214, 217, 218) suitable to yield maximum shear stresses inside the channel (210, 212, 213, 214, 217, 218), and thus enhanced bioburden reduction efficacy. For instance, in one exemplary version, the controller may determine an optimum Fill Time for a given internal channel (210, 212, 213, 214, 217, 218) based on liquid flow rate data provided by flow rate sensor (910), and an optimum Purge Time for the channel (210, 212, 213, 214, 217, 218) based on pressure data provided by pressure sensor (908). In another exemplary version, the controller may determine each of an optimum Fill Time and an optimum Purge Time for a given channel (210, 212, 213, 214, 217, 218) using a respective algorithm that relies on input data provided by both flow rate sensor (910) and pressure sensor (908). In versions in which reprocessing system (900) includes multiple flush valve units (902) and respective flush lines (906) and sensors (908, 910), the system controller may determine a unique Fill Time and a unique Purge Time for each internal channel (210, 212, 213, 214, 217, 218) of endoscope (200), independently, based on data provided by the respective pair of sensors (908, 910) arranged in fluid communication with the internal channel (210, 212, 213, 214, 217, 218).

VI. Treating Multiple Channels of a Device Simultaneously and Asynchronously Via Multi-Way Valve Units As described above, optimizing the bioburden reduction efficacy of a retreatment process for the internal channel of a medical device may be achieved by maximizing the shear stress exerted on the inner walls of the channel by the retreatment liquid. Maximum shear stress may be achieved by filling and purging the channel as quickly as possible. In some instances, the medical device may have multiple internal channels that require treatment, and it may be desirable to complete the fill and purge cycles of those channels simultaneously.

The exemplary systems and methods described below enable filling and purging of multiple internal channels of a device simultaneously, while controlling the filing and purging of each channel independently so as to achieve maximum shear stress and resulting bioburden reduction within the channel.

A. Exemplary Reprocessing System Having 3-Way Valve Units

Figure 15:
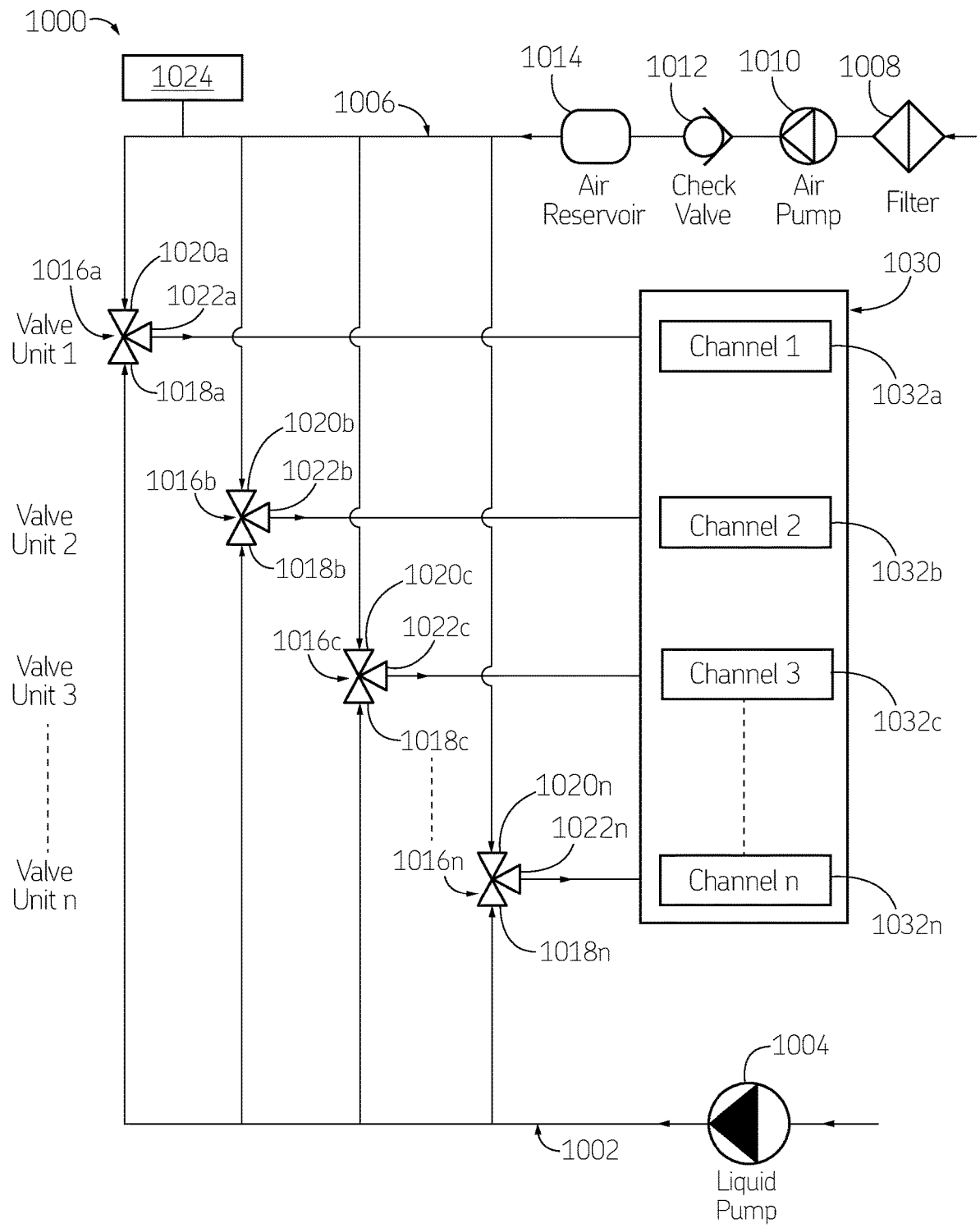
FIG. 15 depicts a schematic diagram of an exemplary reprocessing system operable to fill and purge multiple internal channels of an endoscope simultaneously while controlling the fill and purge time for each internal channel independently via a respective 3-way valve.

FIG. 15 shows a schematic diagram of an exemplary reprocessing system (1000) operable to decontaminate medical devices having internal lumens or channels, such as an endoscope. System (1000) is similar to reprocessing systems (2, 310, 410, 510, 610) described above, except as otherwise described below. As shown, reprocessing system (1000) generally includes a liquid inlet line (1002) comprising a liquid pump (1004). System (1000) further includes an air inlet line (1006) comprising an air filter (1008), an air pump (1010), a check valve (1012), and an air reservoir (1014), connected in series. The components of liquid inlet line (1002) and air inlet line (1004) may be similar in structure and function to any one or more of the corresponding components of reprocessing systems (2, 310, 410, 510, 610) described above. Moreover, while only one liquid pump (1004) and one air pump (1010) are shown in the present version, a plurality of one or both types of pumps (1004, 1010) may be provided in other versions.

Reprocessing system (1000) further includes a plurality of multi-way valve units (1016a-1016n), each of which includes a liquid inlet (1018a-1018n) that fluidly communicates with liquid inlet line (1002), an air inlet (1020a-1020n) that fluidly communicates with air inlet line (1006), and an outlet (1022a-1022n) configured to fluidly communicate with a respective internal channel (1032a-1032n) of a medical device (1030). In the present example, multi-way valve units (1016a-1016n) are shown in the form of 3-way valves. As indicated schematically in FIG. 15, reprocessing system (1000) may include any suitable quantity of 3-way valve units (1016a-1016n) to accommodate any corresponding quantity of internal channels (1032a-1032n) of medical device (1030). Medical device (1030) may be in the form of an endoscope, such as endoscope (200) described above.

Valve unit outlets (1022a-1022n) of reprocessing system (1000) are fluidly isolated from one another such that each valve unit (1016a-1016n) is operable to deliver liquid and pressurized air to its respective device channel (1032a-1032n) independently of every other valve unit (1016a-1016n). One or more actuators (not shown) may be coupled with the moving components of each valve unit (1016a-1016n) to selectively transition the liquid inlet (1018a-1018n), air inlet (1020a-1020n), and/or outlet (1022a-1022n) of each valve unit (1016a-1016n) between respective open and closed states. Such actuators may communicate directly with a controller (1024) of reprocessing system (1000), which may be similar to controller (20) of reprocessing system (2) described above, for example. Controller (1024) may be configured to drive the valve actuators to selectively control each valve unit (1016a-1016n) independently to deliver liquid and pressurized air to the respective internal channel (1032a-1032n) of medical device (1030) for selected durations of time. In some versions, the selected durations of time may be determined using the exemplary methods described above in connection with FIGS. 10-14.

In an exemplary use of reprocessing system (1000), system controller (1024) may command the valve actuators to place each of valve units (1016a-1016n) in an initial channel-filling state in which liquid inlets (1018a-1018n) are open, air inlets (1020a-1020n) are closed, and outlets (1022a-1022n) are open. Controller (1024) may then activate liquid pump (1004) to deliver liquid to internal channels (1032a-1032n) of medical device (1030) via liquid inlets (1018a-1018n) and outlets (1022a-1022n) of the respective valve units (1016a-1016n). Controller (1024) may control each valve unit (1016a-1016n) independently to deliver liquid to the respective device channel (1032a-1032n) for a respective duration of time. For instance, after a first duration of time following the initiation of filling first channel (1032a) has elapsed, controller (1024) may close first liquid inlet (1018a) and open first air inlet (1020a) of first valve unit (1016a). Shortly thereafter, when a second duration of time following the initiation of filling second channel (1032b) has elapsed, controller (1024) may close second liquid inlet (1018b) and open second air inlet (1020b) of second valve unit (1016b). Shortly thereafter, when a third duration of time following the initiation of filling third channel (1032c) has elapsed, controller (1024) may close third liquid inlet (1018c) and open third air inlet (1020c) of third valve unit (1016c). This process may be extrapolated out for device channel (1032n) and corresponding valve unit (1016n). In some instances, each of device channels (1032a-1032n) may be filled for a respective unique duration of time, such that two or more of these durations overlap with one another.

Immediately upon or before opening first air inlet (1020a) of first valve unit (1016a), the controller may activate air pump (1010) to deliver pressurized air to first channel (1032a) of medical device (1030) for purging the liquid from first channel (1032a). Controller (1024) may keep air pump (1010) activated such that when second air inlet (1020b) of second valve unit (1016b) and third air inlet (1020c) of third valve unit (1016c) subsequently open, second and third valve units (1016b, 1016c) may immediately begin directing pressurized air into second and third device channels (1032b, 1032c) for purging. After a fourth duration of time following the initiation of purging first channel (1032a) elapses, controller (1024) may close first air inlet (1020a) of first valve unit (1016a). Similarly, after a fifth duration of time following the initiation of purging second channel (1032b) elapses, controller (1024) may close second air inlet (1020b) of second valve unit (1016b). Similarly, after a sixth duration of time following the initiation of purging third channel (1032c) elapses, controller (1024) may close third air inlet (1020c) of third valve unit (1016c). This process may be extrapolated out for device channel (1032n) and corresponding valve unit (1016n). In some versions, the above-described durations of time for filling and purging each channel (1032a-1032n) of medical device (1030) may be predetermined. In other versions, the fill and purge time durations for each channel (1032a-1032n) may be determined in real-time based on feedback provided by one or more sensors arranged within the channel (1032a-1032n), such as flow rate sensor (708, 910) and/or pressure sensor (808, 908) described above.

Immediately upon or before closing the air inlet (1020a-1020n) of a valve unit (1016a-1016n), controller (1024) may make an independent determination for the respective device channel (1032a-1032n) of whether an additional purge and fill cycle for the channel (1032a-1032n) is required in order to complete a predetermined quantity of cycles. For instance, controller (1024) may determine for first channel (1032a) that an additional cycle is required, and independently determine for second and third channels (1032b, 1032c) that no additional cycles are required. In such case, controller (1024) may close liquid and air inlets (1018b, 1020b, 1018c, 1020c) and/or outlets (1022b, 1022c) of second and third valve units (1016b, 1016c) to terminate reprocessing for second and third channels (1032b, 1032c), and may simultaneously control first valve unit (1016a) in the manner described above to perform an additional fill and purge cycle for first channel (1032a).

As described above, reprocessing system (1000) is operable to treat multiple internal channels (1032a-1032n) of a medical device (1030) simultaneously. Furthermore, system (1000) is configured to apply a unique fill time and a unique purge time for each channel (1032a-1032n), independently of the other channels (1032a-1032n), such that the treatment of two or more of channels (1032a-1032n) may be performed asynchronously. Moreover, the unique fill time and the unique purge time applied for each internal channel (1032a-1032n) may account for a unique inner diameter of the channel (1032a-1032n) relative to one or more of the remaining channels (1032a-1032n). Accordingly, and advantageously, system (1000) may provide an effective bioburden reduction treatment for each internal channel (1032a-1032n) of device (1030) regardless of size differences among channels (1032a-1032n), while completing treatment for device (1030) in a time efficient manner.

B. Exemplary Reprocessing System Having 2-Way Valve Units

Figure 16:
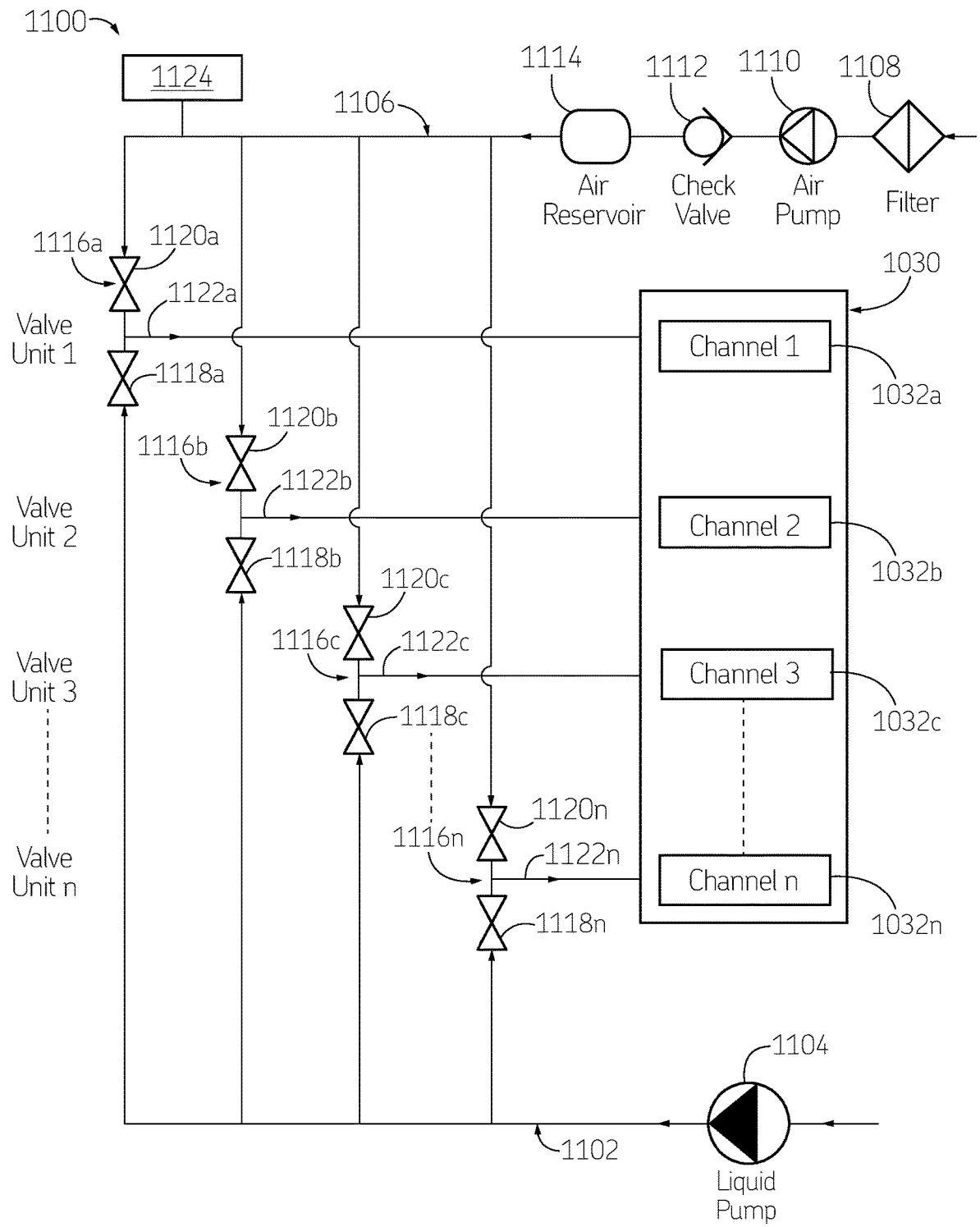
FIG. 16 depicts a schematic diagram of another exemplary reprocessing system operable to fill and purge multiple internal channels of an endoscope simultaneously while controlling the fill and purge time for each internal channel independently via a respective pair of 2-way valves.

FIG. 16 shows another exemplary reprocessing system (1100) operable to treat multiple channels of a medical device simultaneously and asynchronously so as to provide a tailored bioburden reduction treatment for each internal channel, independently. Reprocessing system (1100) is similar to reprocessing system (1000) described above, except as otherwise described below. Similar to reprocessing system (1000), reprocessing system (1100) includes a liquid inlet line (1102) comprising a liquid pump (1104), and an air inlet line (1106) comprising an air filter (1108), an air pump (1110), a check valve (1112), and an air reservoir (1114). System (1100) further includes a plurality of multi-way valve units (1116a-1116n) operable to deliver liquid and pressurized air to internal channels (1032a-1032n) of medical device (1030), as described below.

Unlike valve units (1016a-1016n) of reprocessing system (1000), each valve unit (1116a-1116n) of reprocessing system (1100) comprises a first 2-way valve (1118a-1118n) (or "liquid inlet valve") and a second 2-way valve (1120a-1120n) (or "air inlet valve") that cooperate with one another in the manner generally described below. Liquid inlet valves (1118a-1118n) define respective liquid inlets for valve units (1116a-1116n) that fluidly communicate with liquid inlet line (1102). Air inlet valves (1120a-1120n) define respective air inlets for valve units (1116a-1116n) that fluidly communicate with air inlet line (1106). The liquid inlet valve (1118a-1118n) and corresponding air inlet valve (1120a-1120n) of each valve unit (1116a-1116n) feed into a common valve unit outlet (1122a-1122n). Each valve unit outlet (1122a-1122n) fluidly communicates with a respective internal channel (1032a-1032n) of medical device (1030), and is fluidly isolated from outlets (1122a-1122n) of the remaining valve units (1116a-1116n).

Reprocessing system (1100) further includes a controller (1124) operable to control actuation of the movable components of each valve unit (1116a-1116n) independently of the other valve units (1116a-1116n). More specifically, controller (1124) is operable to control each of the liquid inlet valves (1118a-1118n) independently, and each of the air inlet valves (1120a-1120n) independently. In use, controller (1124) may selectively control the opening and closing of each inlet valve (1118a-1118n, 1120a-1120n) to provide the corresponding internal channel (1032a-1032n) of medical device (1030) with a tailored degree of filling and a tailored degree of purging. For instance, controller (1124) may maintain each of the liquid inlet valves (1118a-1118n) in an open state for a respective unique fill time to fill a respective internal channel (1032a-1032n) of medical device (1030) with liquid. Once a channel (1032a-1032n) has filled, controller (1124) may then close the corresponding liquid inlet valve (1118a-1118n), and then open and maintain the corresponding air inlet valve (1120a-1120n) in an open state for a unique purge time to purge the liquid from channel (1032a-1032n). Controller (1124) may perform this process for each of device channels (1032a-1032n) independently and simultaneously, such that filling and purging of channels (1032a-1032n) is performed asynchronously in manner similar to that described above in connection with reprocessing system (1000). Accordingly, it will be appreciated that reprocessing system (1100) offers at least some of the same advantages as system (1000).

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method for reprocessing an internal channel of a medical device with a reprocessing system having a valve, a fluid line fluidly coupled with the valve, and at least one sensor coupled with the fluid line, the method comprising: (a) performing an actuation of the valve to direct liquid through the fluid line and into the internal channel; (b) while directing the liquid into the internal channel, detecting with the at least one sensor a predetermined condition within the fluid line; (c) in response to detecting the predetermined condition, recording a time duration measured from the actuation of the valve; (d) purging the liquid from the internal channel; and (e) directing liquid through the fluid line and into the internal channel for the time duration.

Example 2

The method of Example 1, wherein the predetermined condition within the fluid line comprises at least one of a flow rate of the liquid within the fluid line or a pressure within the fluid line.

Example 3

The method of any of the preceding Examples, wherein the at least one sensor comprises a flow rate sensor, wherein the predetermined condition within the fluid line comprises a flow rate of the liquid within the fluid line.

Example 4

The method of any of Examples 1 through 2, wherein the at least one sensor comprises a pressure sensor, wherein the predetermined condition within the fluid line comprises a pressure within the fluid line.

Example 5

The method of any of the preceding Examples, wherein detecting the predetermined condition within the fluid line comprises detecting that at least one of a flow rate of the liquid within the fluid line or a pressure within the fluid line has reached a steady state.

Example 6

The method of any of the preceding Examples, wherein purging the liquid from the internal channel comprises purging the liquid for the time duration.

Example 7

The method of any of the preceding Examples, wherein purging the liquid from the internal channel comprises directing one of a second liquid or pressurized air through the fluid line and into the internal channel.

Example 8

The method of any of the preceding Examples, wherein the actuation of the valve comprises a first actuation, wherein the predetermined condition comprises a first predetermined condition, wherein the time duration comprises a first time duration, wherein purging the liquid from the internal channel comprises performing a second actuation of the valve to direct compressed air through the fluid line and to the internal channel, wherein the method further comprises: (a) while directing compressed air to the internal channel, detecting with the at least one sensor a second predetermined condition within the fluid line; (b) in response to detecting the second predetermined condition within the fluid line, recording a second time duration measured from the second actuation of the valve; and (c) after directing liquid through the fluid line and into the internal channel for the first time duration, directing compressed air through the fluid line and to the internal channel for the second time duration to purge the liquid from the internal channel.

Example 9

The method of Example 8, wherein the first predetermined condition within the fluid line comprises one of a flow rate of the liquid within the fluid line or a pressure within the fluid line, wherein the second predetermined condition within the fluid line comprises one of a flow rate of the liquid within the fluid line or a pressure within the fluid line.

Example 10

The method of any of Examples 8 through 9, wherein the first predetermined condition within the fluid line comprises one of a flow rate of the liquid within the fluid line or a pressure within the fluid line, wherein the second predetermined condition within the fluid line comprises the other of a flow rate of the liquid within the fluid line or a pressure within the fluid line.

Example 11

The method of any of Examples 8 through 9, wherein detecting the first predetermined condition within the fluid line comprises detecting that a flow rate of the liquid within the fluid line has reached a steady state after decreasing, wherein detecting the second predetermined condition within the fluid line comprises detecting that a flow rate of the liquid within the fluid line has decreased after the second actuation of the valve.

Example 12

The method of any of Examples 8 through 9, wherein detecting the first predetermined condition within the fluid line comprises detecting that a pressure within the fluid line has reached a steady state after increasing, wherein detecting the second predetermined condition within the fluid line comprises detecting that a pressure within the fluid line has reached a steady state after decreasing.

Example 13

The method of any Examples 8 through 10, wherein detecting the first predetermined condition within the fluid line comprises detecting that a flow rate of the liquid within the fluid line has reached a steady state after decreasing, wherein detecting the second predetermined condition within the fluid line comprises detecting that a pressure within the fluid line has reached a steady state after decreasing.

Example 14

The method of any of Examples 8 through 10 and 13, wherein the at least one sensor comprises a flow rate sensor and a pressure sensor, wherein the flow rate sensor is operable to detect one of the first predetermined condition or the second predetermined condition within the fluid line, wherein the pressure sensor is operable to detect the other of the first predetermined condition or the second predetermined condition within the fluid line.

Example 15

The method of Example 14, wherein detecting the first predetermined condition within the fluid line comprises measuring with the flow rate sensor a flow rate of the liquid within the fluid line, wherein detecting the second predetermined condition within the fluid line comprises measuring with the pressure sensor a pressure within the fluid line.

Example 16

A method for reprocessing first and second internal channels of a medical device with a reprocessing system having a first valve, a second valve, a first sensor, and a second sensor, the method comprising: (a) performing a first actuation of the first valve to direct fluid into the first internal channel; (b) while directing fluid into the first internal channel, detecting with the first sensor a first predetermined condition associated with the fluid; (c) in response to detecting the first predetermined condition, recording a first time duration measured from the first actuation of the first valve; (d) after detecting the first predetermined condition, purging the fluid from the first internal channel; (e) after purging the fluid from the first internal channel, performing a subsequent actuation of the first valve to direct fluid into the first internal channel for the first time duration; (f) while completing step (a), performing a first actuation of the second valve to direct fluid into the second internal channel while directing fluid into the first internal channel; (g) while directing fluid into the second internal channel, detecting with the second sensor a second predetermined condition associated with the fluid; (h) in response to detecting the second predetermined condition, recording a second time duration measured from the first actuation of the second valve; (i) after detecting the second predetermined condition, purging the fluid from the second internal channel; and (j) after purging the fluid from the second internal channel, performing a subsequent actuation of the second valve to direct fluid into the second internal channel for the second time duration.

Example 17

The method of Example 16, wherein the first time duration is different than the second time duration.

Example 18

The method of any of Examples 16 through 17, wherein the first predetermined condition comprises one of a flow rate or a pressure exerted by the fluid being directed into the first internal channel, wherein the second predetermined condition comprises one of a flow rate or a pressure exerted by the fluid being directed into the second internal channel.

Example 19

A method for reprocessing first and second internal channels of a medical device with a reprocessing system having a first pump, a second pump, a first valve unit, and a second valve unit, the method comprising: (a) activating the first pump to direct a first fluid to: (i) a first inlet of the first valve unit, wherein an outlet of the first valve unit is in fluid communication with the first internal channel, and (ii) a first inlet of the second valve unit, wherein an outlet of the second valve unit is in fluid communication with the second internal channel; (b) activating the second pump to direct a second fluid to: (i) a second inlet of the first valve unit, and (ii) a second inlet of the second valve unit; and (c) controlling the first valve unit independently of the second valve unit such that: (i) the first valve unit delivers the first fluid to the first internal channel for a first time duration and subsequently delivers the second fluid to the first channel for a second time duration, and (ii) the second valve unit delivers the first fluid to the second internal channel for a third time duration and subsequently delivers the second fluid to the second channel for a fourth time duration.

Example 20

The method of Example 19, wherein the first internal channel has a first internal diameter and the second internal channel has a second internal diameter different than the first internal diameter, wherein the first time duration is different than the third time duration, wherein controlling the first and second valve units independently comprises controlling the first and second valve units such that the third time duration overlaps a portion of the first time duration.

VIII. Miscellaneous

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. A method for reprocessing first and second internal channels of a medical device with a reprocessing system having a first valve, a second valve, a first sensor, and a second sensor, the method comprising:
 (a) performing a first actuation of the first valve to direct fluid into the first internal channel;
 (b) while directing fluid into the first internal channel, detecting with the first sensor a first predetermined condition associated with the fluid;
 (c) in response to detecting the first predetermined condition, recording a first time duration measured from the first actuation of the first valve;
 (d) after detecting the first predetermined condition, purging the fluid from the first internal channel;

(e) after purging the fluid from the first internal channel, performing a subsequent actuation of the first valve to direct fluid into the first internal channel for the first time duration;

(f) while completing step (a), performing a first actuation of the second valve to direct fluid into the second internal channel while directing fluid into the first internal channel;

(g) while directing fluid into the second internal channel, detecting with the second sensor a second predetermined condition associated with the fluid;

(h) in response to detecting the second predetermined condition, recording a second time duration measured from the first actuation of the second valve;

(i) after detecting the second predetermined condition, purging the fluid from the second internal channel; and (j) after purging the fluid from the second internal channel, performing a subsequent actuation of the second valve to direct fluid into the second internal channel for the second time duration.

2. The method of claim 1, wherein the first time duration is different than the second time duration.

3. The method of claim 1, wherein the first predetermined condition comprises one of a flow rate or a pressure exerted by the fluid being directed into the first internal channel, wherein the second predetermined condition comprises one of a flow rate or a pressure exerted by the fluid being directed into the second internal channel.

4. The method of claim 1, further comprising (a) after detecting the first predetermined condition, holding the fluid in the first internal channel for a first minimum dwell time, and (b) after detecting the second predetermined condition, holding the fluid in the second internal channel for a second minimum dwell time.

5. The method of claim 1, wherein the first sensor comprises a flow rate sensor, and wherein the first predetermined condition comprises a flow rate of the fluid being directed into the first internal channel.

6. The method of claim 1, wherein the first sensor comprises a pressure sensor, and wherein the first predetermined condition comprises a pressure exerted by the fluid being directed into the first internal channel.

7. The method of claim 1, wherein the second sensor comprises a flow rate sensor, and wherein the second predetermined condition comprises a flow rate of the fluid being directed into the second internal channel.

8. The method of claim 1, wherein the second sensor comprises a pressure sensor, and wherein the second predetermined condition comprises a pressure exerted by the fluid being directed into the second channel.

9. The method of claim 1, wherein detecting the first predetermined condition comprises detecting that at least one of a flow rate of the fluid or a pressure of the fluid has reached a steady state.

10. The method of claim 1, wherein detecting the second predetermined condition comprises detecting that at least one of a flow rate of the fluid or a pressure of the fluid has reached a steady state.

11. The method of claim 1, wherein purging the fluid from a select one or both of the first internal channel and the second internal channel comprises directing one of a second fluid or pressurized air through the respective internal channel.

12. The method of claim 1, wherein purging the fluid from a select one or both of the first internal channel and the second internal channel comprises purging the fluid for the first time duration in the case of the first internal channel, or purging the fluid for the second time duration in the case of the second internal channel.

13. The method of claim 1, wherein the first predetermined condition comprises one of a flow rate of the fluid or a pressure of the fluid, wherein the second predetermined condition comprises the other of a flow rate of the fluid or a pressure of the fluid.

14. The method of claim 1, wherein detecting the first predetermined condition comprises detecting that a flow rate of the fluid has reached a steady state after decreasing, wherein detecting the second predetermined condition comprises detecting that a flow rate of the fluid has decreased after the subsequent actuation of the valve.

15. The method of claim 1, wherein detecting the first predetermined condition comprises detecting that a pressure of the fluid has reached a steady state after increasing, wherein detecting the second predetermined condition comprises detecting that a pressure of the fluid has reached a steady state after decreasing.

16. The method of claim 1, wherein detecting the first predetermined condition comprises detecting that a flow rate of the fluid has reached a steady state after decreasing, wherein detecting the second predetermined condition comprises detecting that a pressure of the fluid has reached a steady state after decreasing.

17. The method of claim 1, wherein the fluid comprises a detergent or a disinfectant.

18. The method of claim 1, wherein the method steps are repeated for a predetermined number of cycles.

* * * * *